(12) United States Patent
Winecki

(10) Patent No.: US 12,025,605 B2
(45) Date of Patent: Jul. 2, 2024

(54) OIL RECOVERY SENSOR

(71) Applicant: Battelle Memorial Institute, Columbus, OH (US)

(72) Inventor: Slawomir Winecki, Dublin, OH (US)

(73) Assignee: BATTELLE MEMORIAL INSTITUTE, Columbus, OH (US)

(*) Notice: Subject to any disclaimer, the term of this patent is extended or adjusted under 35 U.S.C. 154(b) by 532 days.

(21) Appl. No.: 17/106,967

(22) Filed: Nov. 30, 2020

(65) Prior Publication Data

US 2021/0080418 A1   Mar. 18, 2021

Related U.S. Application Data

(63) Continuation-in-part of application No. PCT/US2019/033048, filed on May 20, 2019, and a
(Continued)

(51) Int. Cl.
*G01N 33/24* (2006.01)
*G01D 5/24* (2006.01)
(Continued)

(52) U.S. Cl.
CPC .............. *G01N 33/241* (2013.01); *G01D 5/24* (2013.01); *G01F 1/74* (2013.01); *G01F 1/86* (2013.01);
(Continued)

(58) Field of Classification Search
CPC ........ G01R 27/00; G01R 27/02; G01R 27/04; G01R 27/06; G01R 27/26; G01R 27/2605;
(Continued)

(56) References Cited

U.S. PATENT DOCUMENTS 4,916,940 A * 4/1990 Mougne ............... G01N 27/223
73/61.43
5,549,008 A 8/1996 Beauducel et al.
(Continued)

FOREIGN PATENT DOCUMENTS

| JP | H10282033 A | * 10/1998 | ......... G01R 27/2605 |
| WO | WO-9324826 A1 | * 12/1993 | ........... G01N 25/005 |
| WO | WO-2012130112 A1 | * 10/2012 | ............. G01F 23/22 |

OTHER PUBLICATIONS

Abegaz, Brook W. et al., "Measurement and characterization of fluid flow profile using electrical capacitance tomography," IEEE Southeastcon 2014, Mar. 13, 2014, pp. 1-8.
(Continued)

*Primary Examiner* — Hoai-An D. Nguyen
(74) *Attorney, Agent, or Firm* — Lippes Mathias LLP

(57) ABSTRACT

The present disclosure relates to systems and methods for measuring oil/water content in oil-water mixtures, regardless of the salinity of the mixture and regardless of air in the sensor pipe. In some embodiments, the oil content is measured using a dielectric sensor. It is determined whether the oil content is above or below a threshold. If the oil content is above the threshold, the oil content is reported using the measurement from the dielectric sensor. If the oil content is below the threshold, the oil content is reported using the measurement from the eddy current sensor. In some embodiments, which improve performance when there is air in the sensor pipe, two dielectric sensors with different geometries are used instead of the one dielectric sensor.

20 Claims, 19 Drawing Sheets

Related U.S. Application Data continuation-in-part of application No. PCT/US2019/033050, filed on May 20, 2019.

(60) Provisional application No. 62/824,422, filed on Mar. 27, 2019, provisional application No. 62/678,407, filed on May 31, 2018.

(51) Int. Cl.

| | | |
|---|---|---|
| *G01F 1/74* | (2006.01) | |
| *G01F 1/86* | (2006.01) | |
| *G01F 23/263* | (2022.01) | |
| *G01N 27/02* | (2006.01) | |
| *G01N 27/22* | (2006.01) | |
| *G01N 27/90* | (2021.01) | |
| *G01N 33/18* | (2006.01) | |
| *G01N 33/28* | (2006.01) | |
| *G01R 27/06* | (2006.01) | |
| *G01R 27/26* | (2006.01) | |

(52) U.S. Cl.
CPC ......... *G01F 23/263* (2013.01); *G01N 27/023* (2013.01); *G01N 27/221* (2013.01); *G01N 27/227* (2013.01); *G01N 27/90* (2013.01); *G01N 33/1833* (2013.01); *G01N 33/2823* (2013.01); *G01N 33/2847* (2013.01); *G01R 27/06* (2013.01); *G01R 27/2605* (2013.01); *G01N 27/025* (2013.01)

(58) Field of Classification Search
CPC .... G01R 27/2617; G01N 27/00; G01N 27/02; G01N 27/023; G01N 27/025; G01N 27/22; G01N 27/221; G01N 27/227; G01N 27/72; G01N 27/74; G01N 27/82; G01N 27/90; G01N 33/00; G01N 33/18; G01N 33/1826; G01N 33/1833; G01N 33/24; G01N 33/241; G01N 33/26; G01N 33/28; G01N 33/2823; G01N 33/2835; G01N 33/2847; G01D 5/00; G01D 5/12; G01D 5/14; G01D 5/24; G01F 1/00; G01F 1/74; G01F 1/76; G01F 1/86; G01F 23/00; G01F 23/22; G01F 23/26; G01F 23/263
USPC .................. 324/600, 649, 658, 663, 664
See application file for complete search history.

(56) References Cited

U.S. PATENT DOCUMENTS

| | | | |
|---|---|---|---|
| 7,201,068 | B2 | 4/2007 | Foss et al. |
| 10,481,129 | B1 | 11/2019 | Winecki et al. |
| 10,509,003 | B2* | 12/2019 | Vogt ...................... G01N 27/08 |
| 10,591,441 | B2 | 3/2020 | Winecki et al. |
| 10,620,161 | B2 | 4/2020 | Winecki et al. |
| 2005/0040045 | A1* | 2/2005 | Nilsen ................... B01D 17/06 |
| | | | 204/660 |
| 2013/0144548 | A1 | 6/2013 | Xie |
| 2018/0010448 | A1* | 1/2018 | Hay .................... E21B 17/0285 |

OTHER PUBLICATIONS

Demori, M. et al., "A sensor system for oil fraction estimation in a two phase oil-water flow," Procedia Chemistry, Elsevier, Amsterdam, NL, vol. 1, No. 1, Sep. 1, 2009.

Gustavo Villares et al., "A non-linear Model of Sensitivity Matrix for Electrical Capacitance Tomography Smart air bags," http://www.electrostatics.org/images/ESA2012_R4.pdf, Apr. 1, 2012.

Jaworek A. et al., "Capacitance sensor for void fraction measurement in water/steam flows," Flow Measurement and Instrumentation, Butterworth-Heinemann, Oxford, GB, vol. 15, No. 5-6, Oct. 1, 2004, pp. 317-324.

Pagano, Daniel J., Water Fraction Measurement Using a RF Resonant Cavity Sensor, 19th Symposium IMEKO TC 4 Symposium and 17 IWADC Workshop Advances in Instrumentation and Sensors Interoperability, Jul. 19, 2013.

Wylie, S R et al., "RF sensor for multiphase flow measurement through an oil pipeline", presented at 13th International Conference on Sensors held in Chatham, Kent, on Sep. 6-7, 2005.; RF sensor for multiphase flow measurement through an oil pipeline, Measurement Science and Technology, IOP, Bristol, GB, vol. 17, No. 8, Aug. 1, 2006.

Qu, Zilian et al., "Online measurement of water concentration of oil-water mixtures in the flow of pipeline by using eddy current me", Measurement Science and Technology, IOP, Bristol, GB, vol. 24, No. 12, Nov. 12, 2013.

International Search Report from PCT Application No. PCT/US2019/033050 dated Dec. 5, 2019.

International Search Report from PCT Application No. PCT/US2019/033048 dated Nov. 5, 2019.

Texas Instruments, FDC2114 and FDC2214 Evm User's Guide, Literature No. SNOU138A, Jun. 2015—Revised Oct. 2016.

Texas Instruments, FDC2x1x EMI-Resistant 28-Bit, 12-Bit Capacitance-to-Digital Converter for Proximity and Level Sensing Applications, Literature No. SNOSCZ5A, Jun. 2015, Revised Jun. 2015.

Delahay, Paul, Louisiana State University, "New Instrumental Methods in Electrochemistry" Interscience Publishers, Inc., New York, Interscience Publishers Ltd., London, 1954, Ch. 15, pp. 319-345.

\* cited by examiner

| Fluid inside of sensor pipe | Capacitance measured by FDC2214 |
|---|---|
| Empty pipe | 28.906 |
| Mineral oil | 28.953 |
| 1 wt% NaCl solution | 46.790 |
| 5 wt% NaCl solution | 52.804 |

OIL RECOVERY SENSOR

CROSS-REFERENCE TO RELATED APPLICATIONS

This application is a continuation-in-part (CIP) of International Application PCT/US2019/033050 filed May 20, 2019 which claims the benefit of U.S. Provisional Application No. 62/824,422 filed Mar. 27, 2019. This application is also a continuation-in-part (CIP) of International Application PCT/US2019/033048 filed May 20, 2019 which claims the benefit of U.S. Provisional Application No. 62/678,407 filed May 31, 2018. International Application PCT/US2019/033050 filed May 20, 2019 is incorporated herein by reference in its entirety. International Application PCT/US2019/033048 is incorporated herein by reference in its entirety. U.S. Provisional Application No. 62/824,422 filed Mar. 27, 2019 is incorporated herein by reference in its entirety. U.S. Provisional Application No. 62/678,407 filed May 31, 2018 is incorporated herein by reference in its entirety.

BACKGROUND

The present disclosure relates to systems and methods for determining the oil/water content of oil-water mixtures.

According to the U.S. Department of Energy, 1.3 million gallons (4.9 million liters) of petroleum are spilled into U.S. waters from vessels and pipelines in a typical year. A major oil spill could easily double that amount. Generally, mechanical surface skimmers remove oil and oil-water mixtures from surface water.

Present systems for measuring oil content in oil-water mixtures encounter difficulties when the oil-water mixture has high electrical conductivity, as can occur with seawater or any highly saline water found in industrial or oil and gas applications. In addition, present systems encounter difficulties when there is air in the sensor pipe. It would be desirable to provide systems and methods that address these difficulties.

BRIEF DESCRIPTION

The present disclosure provides systems and methods for measuring the oil/water content of oil-water mixtures, regardless of the presence of air in the sensor pipe or salinity of the water in the mixture. Briefly, to account for air in the pipe, two dielectric sensors with two different geometries are used. In addition, to account for salinity in the water, an eddy current sensor may be advantageously combined with the dielectric sensors. The dielectric sensors are used if the oil content is above a threshold value, which may be the transition point between oil-in-water and water-in-oil mixtures or emulsions, and the eddy current sensor is used if the oil content is below the threshold value. Computer programs and systems for determining which sensor measurement is more accurate are also described herein.

In accordance with one aspect of the present application, systems for measuring the oil content of a fluid are disclosed. The system may include a horizontal pipe having a cavity configured to hold air, oil, and water. The system may further include a first dielectric sensor, comprising: a first electrode on a first side of the pipe; and a second electrode on a second side of the pipe, wherein the first side of the pipe is opposite the second side of the pipe. The system may further include a second dielectric sensor, comprising: a first electrode on a top of the pipe; and a second electrode on a bottom of the pipe.

In some implementations, an inner surface of the top of the pipe is in contact with the air; an inner surface of the bottom of the pipe in in contact with the water; an inner surface of the first side of the pipe is contact with all of the air, the oil and the water; and an inner surface of the second side of the pipe is contact with all of the air, the oil and the water. In some embodiments, the system further includes an eddy current sensor, comprising: a resonance circuit formed by a capacitor, and an inductor configured to produce a magnetic field within the cavity; and a SWR analyzer configured to measure a height of a peak of a resonance frequency of the resonance circuit. In some implementations, the system further includes one or more processors configured to determine if the oil content is above or below a threshold; and if the oil content is above the threshold, report the oil content using the first and second dielectric sensors; and if the oil content is below the threshold, report the oil content using the eddy current sensor.

In some embodiments, the system includes one or more processors configured to approximate a water fraction w in the pipe according to the equation: $w=a_1+a_2f_1+a_3f_1^2$, wherein $a_1$, $a_2$, $a_3$ are constant parameters, and $f_1$ is a frequency measured by the first dielectric sensor with the electrodes attached to both sides of the sensor cavity. In some embodiments, the one or more processors are further configured to approximate an oil o fraction using the equation: $o=b_1+b_2w+b_3f_2+b_4wf_2+b_5w^2+b_6f_2^2+b_7f_2^3$ wherein $b_1$, $b_2$, $b_3$, $b_4$, $b_5$, $b_6$, $b_7$ are adjustable parameters, and $f_2$ is a frequency measured by the second dielectric sensor with the electrodes attached to bottom and top of the sensor cavity.

In some implementations, the system includes one or more processors configured to approximate a water fraction in the pipe using a first frequency measured by the first dielectric sensor. In some implementations, the one or more processors are further configured to approximate an oil fraction in the pipe using: (i) the approximated water fraction in the pipe, and (ii) a second frequency measured by the second dielectric sensor. In some implementations, the system further includes a display configured to display the approximated oil fraction.

In another aspect, there is a method for measuring oil content of a fluid, including measuring a first frequency with a first dielectric sensor, wherein the first dielectric sensor comprises: a first electrode on a first side of the pipe; and a second electrode on a second side of the pipe, wherein the first side of the pipe is opposite the second side of the pipe. The method may further include measuring a second frequency with a second dielectric sensor, wherein the second dielectric sensor comprises: a first electrode on a top of the pipe; and a second electrode on a bottom of the pipe.

In some implementations, an inner surface of the top of the pipe is in contact with air; an inner surface of the bottom of the pipe is in contact with water; an inner surface of the first side of the pipe is contact with all of the air, oil and the water; and an inner surface of the second side of the pipe is contact with all of the air, the oil and the water.

In some implementations, the method further includes using the first frequency to approximate a water fraction in the pipe. The method may further include approximating an oil fraction in the pipe using (i) the approximated water fraction, and (ii) the second frequency. The method may further include displaying the approximated oil fraction on a display.

In yet another aspect, there is a system for measuring oil content of a fluid. The system comprises at least one processor; and at least one memory including computer program code. The at least one memory and the computer program code is configured to, with the at least one processor, cause the system at least to: with a first dielectric sensor, measure a first frequency of the fluid in a pipe, wherein the first dielectric sensor comprises: a first electrode on a first side of the pipe; and a second electrode on a second side of the pipe, wherein the first side of the pipe is opposite the second side of the pipe; and with a second dielectric sensor, measure a second frequency the fluid, wherein the second dielectric sensor comprises: a first electrode on a top of the pipe; and a second electrode on a bottom of the pipe.

In some implementations, an inner surface of the top of the pipe is in contact with air; an inner surface of the bottom of the pipe in in contact with water; an inner surface of the first side of the pipe is contact with all of the air, oil and the water; and an inner surface of the second side of the pipe is contact with all of the air, the oil and the water.

In other embodiments, the at least one processor is configured to execute the computer-readable instructions to cause the system to use the first frequency to approximate a water fraction in the pipe. In further embodiments, the at least one processor is configured to execute the computer-readable instructions to cause the system to approximate an oil fraction in the pipe using (i) the approximated water fraction, and (ii) the second frequency. In still further embodiments, the at least one processor is configured to execute the computer-readable instructions to cause the system to display the approximated oil fraction on a display.

Advantageously, the systems and methods described herein have the ability to accurately monitor and report oil-water percentages from 0 to 100% regardless of water salinity. By way of comparison, traditional dielectric sensors cannot work with high electrical conductivity mixtures, for instance seawater-based mixtures that contain more than ~30% of sea water. The disclosed approaches work with water of any salinity that is relatively stable (i.e. does not change quickly over time). This includes fresh water, and seawater from different seas, even if very concentrated.

Advantageously, in the approaches described herein, the response is independent of oil-water dispersion, including mixtures that are not homogeneous, homogenous, or an emulsion. In particular, the sensor system can provide accurate results whether the oil-water mixture is an oil-in-water mixture or a water-in-oil mixture.

The sensing system can also operate with an open pipe of any size serving as the sensor cavity. In addition, there is no need to install a flow conditioning device upstream or downstream of the sensor(s). For instance, there is no need for a homogenizer, which generally are not a good option for oil skimming operations as they become quickly clogged during operations and increase pressure drop.

The sensor system measurement can also be carried out at any pressure. The sensor system can also reliably detect the sensor cavity being empty. Metal electrodes do not need to make physical contact with the oil-water mixture to be tested. Advantageously, the sensor uses very minimal power. The measurement can be realized with as little as 0.1 mW of power, not counting power needed for a processor or communication electronics. The sensor system can be certified as meeting ATEX Level 2 criteria (for use in potentially explosive atmospheres).

These and other non-limiting aspects of the present disclosure are described in more detail below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
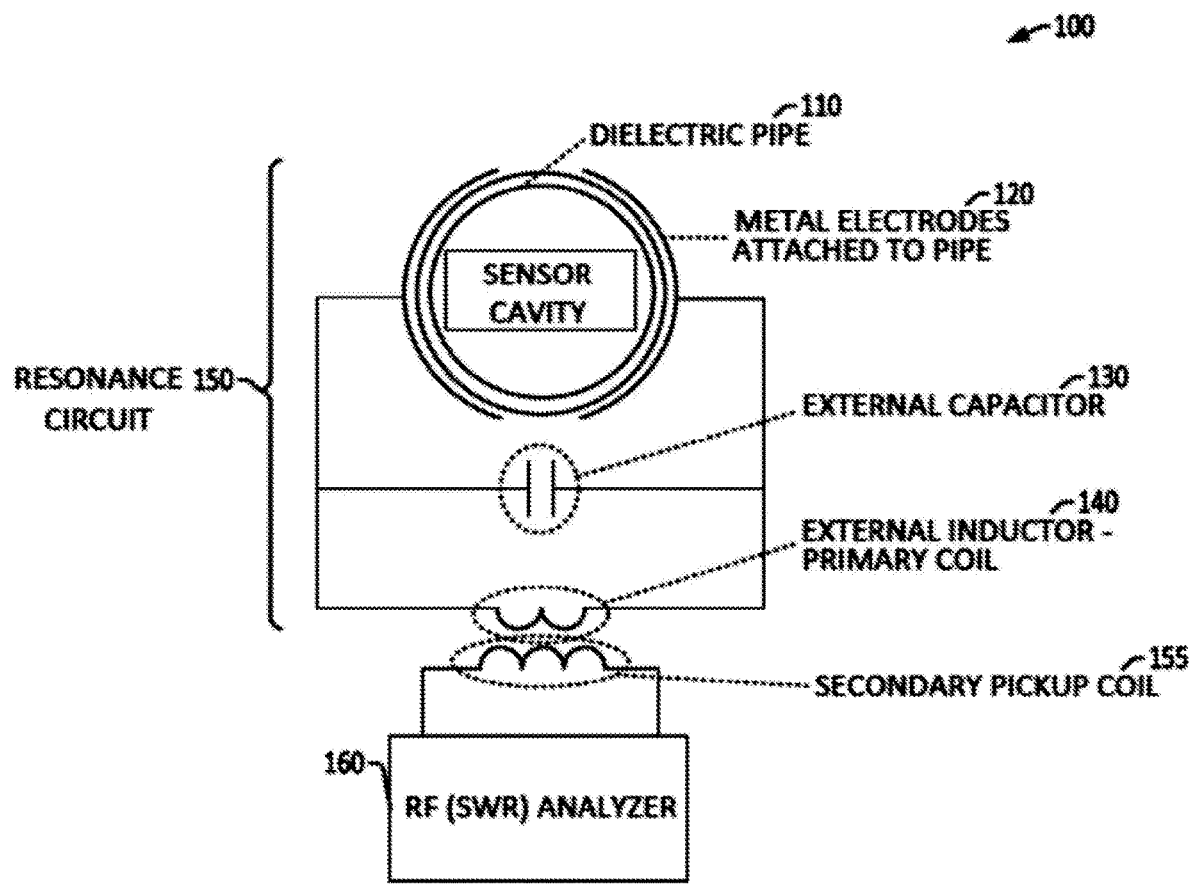
FIG. 1 illustrates a dielectric sensor.

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

The term "comprising" is used herein as requiring the presence of the named components/steps and allowing the presence of other components/steps. The term "comprising" should be construed to include the term "consisting of", which allows the presence of only the named components/steps.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

The modifier "about" used in connection with a quantity is inclusive of the stated value and has the meaning dictated by the context. When used in the context of a range, the modifier "about" should also be considered as disclosing the range defined by the absolute values of the two endpoints. For example, the range of "from about 2 to about 10" also discloses the range "from 2 to 10." The term "about" may refer to plus or minus 10% of the indicated number. For example, "about 10%" may indicate a range of 9% to 11%, and "about 1" may mean from 0.9-1.1.

The present application is related to oil-water mixtures. It should be understood that the oil content plus the water content generally equals 100% (solutes and other materials in the fluid not being considered).

Dielectric sensors may be used to measure water content in oil-water mixtures, gas-water mixtures, and moisture levels in solids. The principle of measurement is related to the large value of water's relative dielectric constant (permittivity), which is about 80. This value is much greater than the dielectric constant of gases (close to 1), organic liquids (like oils and crudes) as well as solids (below about 10).

Dielectric sensors are generally constructed as capacitors that contain a cavity that is filled with the oil-water mixture. The cavity can be either a flow through device (e.g. a tube or pipe) or a batch device (e.g. a vessel or tank). The flow through device or batch device may have electrodes placed on either side of it. The dielectric sensor detects changes in electrical capacitance caused by different water content of the fluid in the cavity. Such changes are detected by a direct capacitance measurement, or often by a detection of a frequency shift of a resonance circuit which includes the cavity itself.

However, the dielectric measurement is not reliable when the mixture being measured is highly electrically conductive, for instance seawater or any highly saline water found in industrial or oil and gas applications. The high conductivity of the mixture can be represented in the dielectric sensor as a low resistance connected in parallel with the cavity's capacitance which effectively shortens the cavity. This effect cannot be solved by modifying the shape or size of the cavity in which the fluid/mixture is measured, since the relative contribution of the cavity's capacitance and resistance is geometry-independent. Theoretically, the relative resistance contribution can be reduced by increasing the frequency of the dielectric measurement, since the capacitance contribution is increased at higher frequencies, while the resistive contribution remains constant. However, a frequency increase causes reduction of skin depth, which determines the extent of penetration of electromagnetic waves into the tested mixture. This decrease in skin depth penetration makes a sensor sensitive only to areas close to its electrodes, which may be a small fraction of overall sensor volume, especially for larger sensors. Due to the high salinity of typical seawater, the conductivity effect is severe enough to prevent successful development of dielectric sensors that by themselves are effective in marine environments. In the case of oil-water sensors operating with seawater, dielectric sensors are capable of measuring oil content only for low conductivity, water-in-oil mixtures/emulsions that contain a minimum of 60-70% oil.

The systems and methods described herein relate to sensor configurations capable of measuring the oil or water content of oil-water mixtures. The measurements are accurate even in cases where the water contains large amounts of salt, for example seawater. Very generally, measurement are made using: (1) a dielectric measurement, and (2) an eddy current loss measurement. The dielectric measurement may be used for high oil content mixtures/emulsions that are of the water-in-oil type, and therefore have relatively low electrical conductivity. For this type of mixture/emulsion, the dielectric sensor provides a reliable measurement for oil content. On the other hand, the eddy current measurement is used for low oil content mixtures/emulsions that are of the oil-in-water type and have high electrical conductivity. For this type of mixture/emulsion, the eddy current measurement provides a reliable measurement for oil content. The measurements can be compared to a reference table that accounts for oil content and salinity, etc. Using both sensors in the implementations as described herein allows for unambiguous and accurate measurement of oil or water content for a broad range of oil-water mixtures including mixtures of crude oils and/or mixtures with saline water.

The systems and methods described herein provide a reliable oil content measurement for a broad range of mixtures ranging from including pure saline water to pure oil. In one aspect, the device works at different water salinities and for different oil and crude types, and is insensitive to oil-water dispersion state. The sensors can be used in any application where oil-water mixtures need to be evaluated for oil content or water cut. One application of the sensor systems described herein is for offshore applications, for instance for evaluation of efficiency of oil recovery during spill clean-up operations.

The sensors can be operated at relatively high operating frequencies, from 1 MHz up to 1 GHz, which minimizes concerns related to electrode polarization. The proposed sensors also provide a relatively uniform sensitivity across a pipe cross section, which allows for use of open pipes with a broad diameter range, without any mixing or homogenizing devices while still obtaining accurate measurements.

FIG. 1 presents a design of a dielectric sensor 100, which is used in some embodiments of the present disclosure. The sensor is installed on a cavity 110 that contains the fluid whose oil/water content will be measured. The cavity itself can be considered part of the sensor system. The cavity is illustrated here as a pipe or tube through which fluid can flow. The cavity can be made of any suitable material, for example acrylic or PVC. The cavity may have any desired diameter. In experiments reported further herein, the cavity has a diameter of 3 inches. A pair of electrodes 120 is attached to the cavity 110. The electrodes are made of a suitable metal. The electrodes are usually attached to the exterior of the cavity 110. Together, the cavity and electrodes act as a capacitor, whose capacitance will change depending on the fluid in the cavity that is being measured.

The dielectric sensor 100 also includes a first capacitor 130 and a first inductor 140. The first capacitor may have a capacitance of about 10 picofarads (pF) to about 100 pF. The first inductor may have an inductance of about 0.1 microhenrys (pH) to about 2 µH. The electrodes 120, the first capacitor 130, and the first inductor 140 are connected to each other in parallel, i.e. in a parallel circuit. Together, these components form a first resonance circuit 150.

A secondary pickup coil 155 is installed proximate the first inductor 140, and connected to a first radio frequency Standing Wave Ratio (SWR) analyzer 160. The first SWR analyzer is used to identify the peak resonance frequency of the first resonance circuit. Examples of suitable SWR analyzers include the AA-170 and AA-1400, both produced by Rig Expert. If desired, a different device or method can be employed to measure the resonance peak. For instance, a frequency counter or AC modulation-demodulation circuit can be used to determine the resonance frequency. The distance between the first inductor and the secondary pickup coil can be adjusted to optimize the sharpness of the resonance peak. The SWR analyzer will scan an operating frequency range, desirably near the expected resonance frequency. The resonance frequency, defined by a maximum peak, is recorded for the oil-water mixture.

The sensor systems of the present disclosure also include an eddy current sensor. An eddy current measurement is effective for measuring the oil/water content in oil-in-water mixtures, while free of the electrical conductivity measurement drawbacks present in the dielectric sensor. The eddy current effect is observed in all conductive materials that are exposed to changing magnetic fields. Eddy currents are electrical currents that cause two effects: (1) they have an orientation and intensity that tends to cancel the external magnetic field that generates them, and (2) they cause energy losses due to heat generation in the conductive media. In fact, the eddy currents are responsible for the finite skin depth penetration of electromagnetic waves in conductive media. Energy losses due to eddy currents allow for measurement of this effect by means of a resonance circuit. If the inductor generating the eddy current effect is a part of the resonance circuit, eddy current energy losses in the tested material will cause losses in the resonance circuit. These losses will cause broadening and height reduction of a resonance peak, both easily measurable effects.

Figure 2:
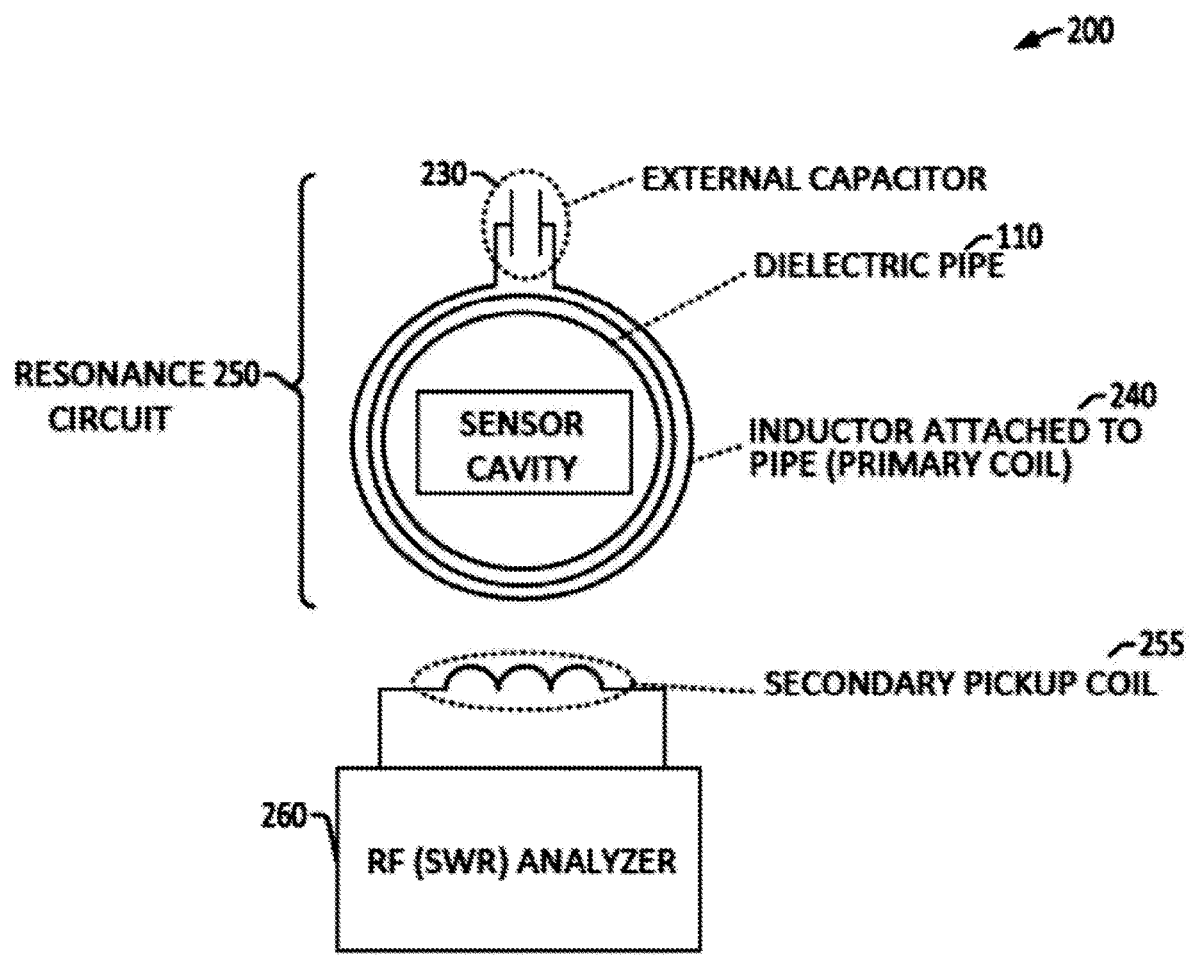
FIG. 2 illustrates an eddy current sensor.

FIG. 2 illustrates an eddy current sensor 200. A second inductor 240 is attached to the cavity 110 in a manner that exposes the oil-water mixture within the cavity to a magnetic field. Desirably, the second inductor 240 is in the form of a coil wound around the cavity 110, as this ensures the most uniform sensitivity across the entire cross section of the cavity. Preferably, the coils of the second inductor are on the exterior of the cavity, and are not in direct electrical contact with the tested fluid within the cavity, since this would introduce direct conductivity effects and result in additional measuring problems. The coils of the inductors described in the present disclosure can be made from any suitable conductive metal, copper being the most suitable.

The second inductor 240 is connected to a second capacitor 230 and forms a second resonance circuit 250. The second inductor and the second capacitor are arranged in series with each other. The second capacitor 230 may have a capacitance of about 50 to about 700 pF, including from about 100 pF to about 300 pF. The second inductor may have an inductance of about 0.1 microhenrys (pH) to about 2 µH.

A secondary pickup coil 255 is installed proximate the second inductor 240, and connected to a second radio frequency Standing Wave Ratio (SWR) analyzer 260. This configuration for the eddy current sensor has a resonance frequency of about 21.72 megahertz (MHz). The second SWR analyzer is used to identify the magnitude of the resonance peak, which correlates with the oil/water content of the fluid within the cavity. Again, examples of suitable SWR analyzers include the AA-30, AA-170 and AA-1400, all produced by Rig Expert. The distance between the second inductor and the secondary pickup coil can be adjusted to optimize their coupling and the sharpness of the resonance peak.

It has been found that the measurement of the dielectric sensor(s) is most accurate for oil-water mixtures having an oil content above a threshold value, while the measurement of the eddy current sensor is most accurate for oil-water mixtures having an oil content below the threshold value. In one embodiment, the threshold value can be an oil content of 70 percent. In other embodiments, the threshold value can be an oil content corresponding to a resonance frequency that allows for distinction between oil-in-water mixtures and water-in-oil mixtures (this resonance frequency may vary depending on the values of the capacitor and inductor used in the dielectric sensor). Thus, a system using both dielectric and eddy current sensors is expected to be most accurate over the entire range of possible oil/water values. The measurements made by the respective sensor can be compared to reference tables to determine the oil content.

A system using both types of measurements can be built with the cavity in the form of a single pipe or tube through which the oil-water mixture flows, with the two sensors being mounted on the single pipe and spaced apart from each other. The two measurements (by the dielectric sensor(s) and the eddy current sensor) can be performed simultaneously or in short succession. It is expected that two simultaneous and continuous measurements will be possible with proper selection of operating frequencies that do not overlap, including harmonics overlap. Both measurements require very small power; the SWR analyzer used in both sensors has an output power of −10 dBm, which is equivalent to 0.1 mW, not counting power needed for a processor and communication electronics.

Figure 3:
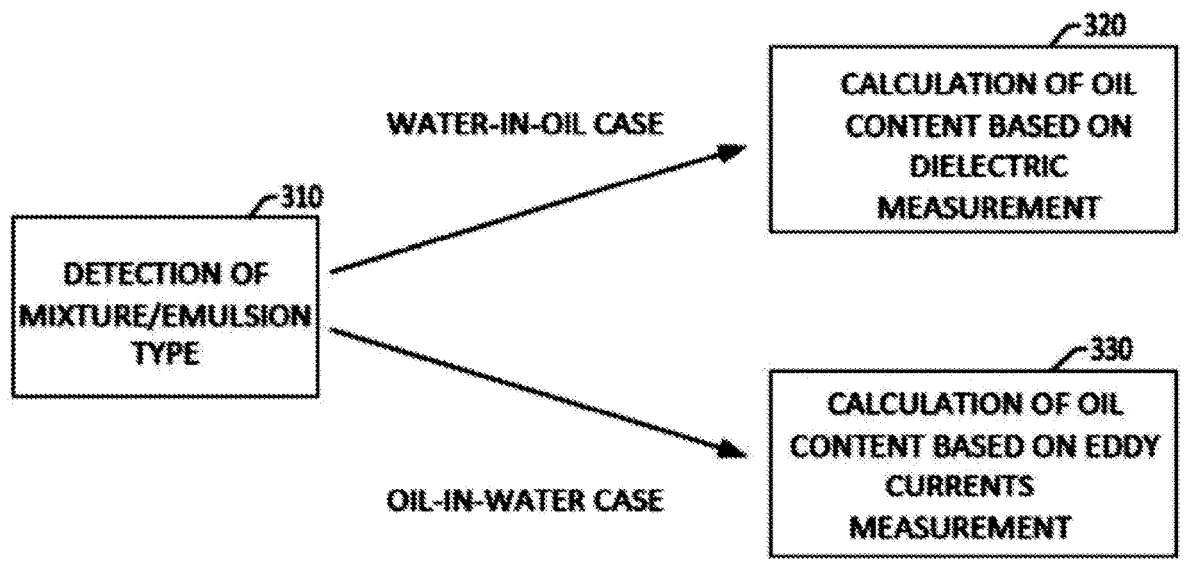
FIG. 3 shows components of an algorithm for calculation of oil/water content based on combined dielectric and eddy current measurements.

FIG. 3 schematically illustrates an algorithm that can be used to report an accurate measurement of the oil/water content. The first part 310 of the algorithm identifies what type of mixture or emulsion is filling the sensor cavity. This can be determined by the resonance frequency obtained by the dielectric sensor. For instance, an oil-in-water emulsion is identified if the resonance frequency is less than a given value (which is affected by the capacitor and inductor values), and a water-in-oil emulsion is identified if the resonance frequency is above this value. This determines whether the reported oil/water content is based on the measurement from the dielectric sensor or the eddy current sensor. If the oil-water mixture is a water-in-oil emulsion, the measurement from the dielectric sensor 320 is reported. If the oil-water mixture is an oil-in-water emulsion, the measurement from the eddy current sensor 330 is reported.

Figure 4:
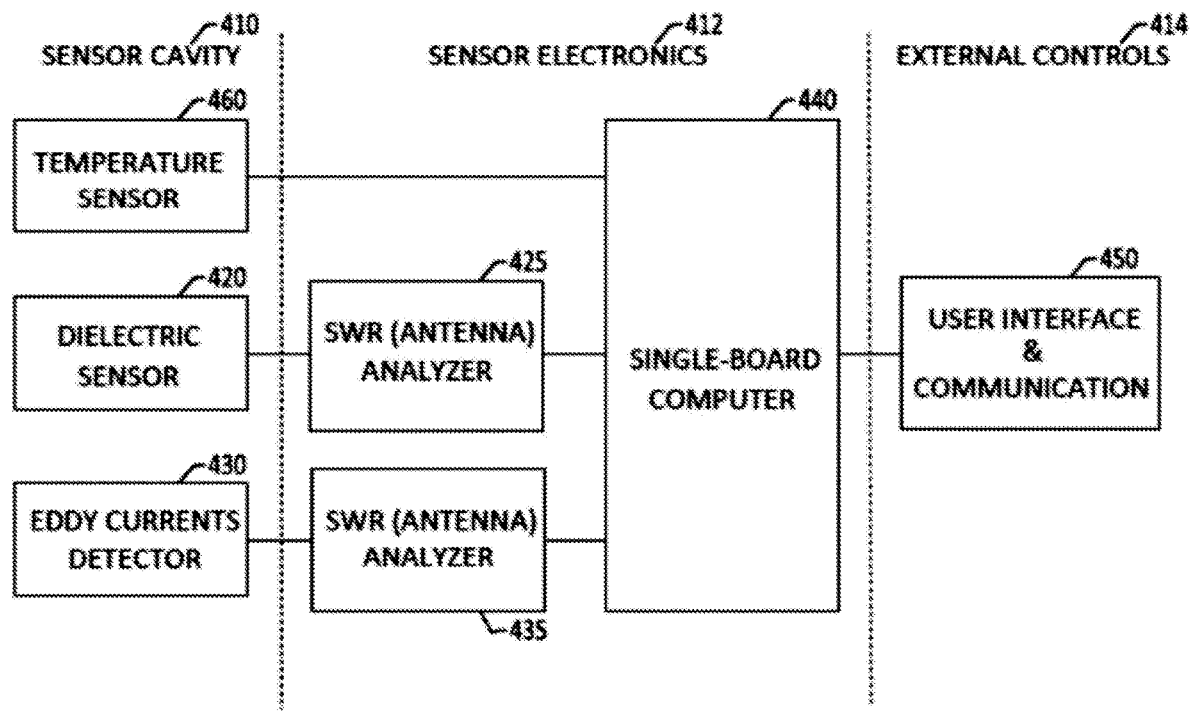
FIG. 4 is a diagram of an exemplary embodiment of a sensor system that includes SWE analyzers and a single-board computer.

FIG. 4 is a block diagram illustrating an exemplary embodiment of a sensor system of the present disclosure. The sensor system 400 includes components that are proximate the sensor cavity 410, electronics 412 for processing the measurements made by the sensors, and external controls 414. The components proximate the sensor cavity 410 include the dielectric sensor 420, the eddy current detector 430, and a temperature sensor 460 that is used to account for changes in water conductivity due to temperature. As described above, the components of the dielectric sensor 420 and the eddy current detector 430 are external to the sensor cavity, and do not need to contact the oil-water mixture that is present within the sensor cavity. The electronics 412 include the first SWR analyzer 425 for the dielectric sensor 420 and the second SWR analyzer 435 for the eddy current detector 430. A single board computer 440 is used to control the SWR analyzers, carry out algorithm calculations, and handle input and output operations. For example, the single board computer can compare the sensor measurements to reference tables or databases that identify the oil/water content based on the measurements made by the dielectric sensor and/or the eddy current sensor.

The SWR analyzer(s) can scan a preselected frequency range anywhere from a fraction of a megahertz up to tens, or for some units, hundreds of megahertz. SWR analyzers are available as handheld instruments with a simple keyboard and a display. Selected SWR analyzers, for instance the AA-30 ZERO analyzer, are intended to be imbedded in larger instruments, and are constructed as a single electronic board without peripherals. These SWR analyzers use serial or USB ports for external communication and control. The output power of SWR analyzers is very small, on the order of milliwatts, which is sufficient for the present application.

In some embodiments, two RigExpert AA-30 ZERO single-board analyzers are used for the sensors. A Beagle-Bone Black open-source single-board computer can be used to control the SWR analyzers, carry out algorithm calculations, and handle input and output operations. The Beagle-Bone Black provides direct and simultaneous control of two AA-30 analyzers plus one temperature sensor, on-board storage of oil fraction data, and hosting of a website used for user interface.

For the dielectric sensor(s), operating frequencies below 10 MHz should be avoided because of electrode and oil-water interface polarization effects. Generally, any operating frequency in the range of about 10 MHz to about 300 MHz can be used. Other operating frequency ranges include about 40 MHz to about 270 MHz, and about 20 MHz to about 24 MHz. Skin depth consideration does not significantly affect the dielectric measurement, due to very low conductivities of water-in-oil mixtures.

For the eddy current sensor, operating frequencies below 10 MHz should also be avoided because of electrode and oil-water interface polarization effects. The operating frequency should be selected to provide effective dynamic range of the eddy current measurement. Two frequency selection methods can be used. First, the operating frequency is selected to be the maximum frequency, which allows for reliable eddy current height measurement for pure water with maximum salinity expected for a given sensor and electronic implementation. Second, the operating frequency is selected to provide a pure water skin depth penetration close to a radius of the sensor cavity. This can be determined according to the following Equation (1):

$$f(\text{MHz}) = 2500/(R^2 \sigma) \quad (1)$$

where R is the radius of the sensor cavity in cm, and σ is the conductivity of the fluid in S/m. For instance, for seawater with conductivity of 5 S/m and a pipe that is 4 inches in diameter, the operating frequency of the order of 19 MHz may be appropriate. In some particular embodiments, the operating frequency for the eddy current sensor is from about 15 MHz to about 16 MHz.

Overlap between the operating frequencies of the dielectric sensor and the eddy current sensor, including their harmonics, should be avoided to prevent signal interference.

The physics of the eddy current effect can be affected by the salinity of the water. Thus, various embodiments described herein account for water salinity. This can be realized, for example, by calibration of the sensor system performed with pure water having a given salinity, or by directly entering the salinity value into the sensor. This permits the appropriate reference tables/databases to be used to identify the oil/water content based on the sensor measurements.

If there are no significant interactions between the oil and water, the electrical conductivity of the oil-water mixture ($C_{Mixture}$) can be expressed as the product of the pure saline water electrical conductivity ($C_{water}$) and a geometrical factor (g), which accounts for presence of oil in the water, as shown in Equation (2) below.

$$C_{Mixture} = C_{Water} \times g \quad (2)$$

The pure saline water conductivity ($C_{water}$) is a function of water salinity and temperature, and its value can be calculated using published correlations. The geometrical factor (g) is a function of oil volume fraction, and oil-water dispersion. Experiments carried out with different oil types, various oil-in-water mixtures and emulsions, and frequencies in megahertz range (10-50 MHz) indicate that equation 1 above can be approximately solved by the following Equation (3).

$$\text{Oil fraction} \approx A\left(1 - \frac{C_{Mixture}}{C_{Water}}\right) \quad (3)$$

where A is a constant, and is between 60% and 70%. The mixture conductivity ($C_{Mixture}$), measured by the eddy current sensor, is a monotonic function of the eddy peak height, which can be determined by suitable sensor calibration procedure. Importantly, the oil fraction measurement based on Equation (3) is not sensitive to the homogeneity of the oil-water dispersion, and can be used with both coarse mixtures and stable emulsions.

In some embodiments, the sensor systems described herein are specifically designed to meet the needs of the oil recovery industry. Currently, there is no way for ships of opportunity to know the ratio of oil to water in skimming operations. The disclosed sensor systems of this present disclosure will solve that problem. The approaches described herein save operators money by reducing storage of seawater and increasing space for recovered oil. Furthermore, the approaches described herein will allow for fewer trips between recovery vessels and storage barges, and will further result in reduced cost for waste processing and filtering of seawater. These sensor systems will help improve efficiency and reduce the amount of seawater that must be processed, thereby reducing operating costs.

The systems and methods described herein may also be used in oil processing and as an oil cut sensor or water cut sensor for wells producing crude-ground water mixtures.

The systems described herein have the ability to monitor oil-water percentages from 0% to 100% regardless of water salinity. In addition, the sensitivity of the sensor system is very uniform across the sensor cavity, making the sensor system independent of the oil-water dispersion, including mixtures that are not homogeneous, homogenous, or in an emulsion state.

The techniques described herein are suitably implemented in the form of one or more electronic processors executing instructions read from a non-transitory storage medium such as a hard drive or other magnetic storage medium, an optical disk or other optical storage medium, a cloud-based storage medium such as a RAID disk array, flash memory or other non-volatile electronic storage medium, or so forth. Some embodiments also include computers connected via an electronic network (e.g. WiFi, Ethernet, Internet, various combinations thereof, or so forth) to form a parallel computing resource, ad hoc cloud computing resource, or so forth.

The following examples are provided to illustrate the systems and methods of the present disclosure. The examples are merely illustrative and are not intended to limit the disclosure to the materials, conditions, or process parameters set forth therein.

Examples

Two sections of 3-inch schedule 40 acrylic pipes were connected to form a closed loop fluid recirculation system able to pump mixtures of oil and saline water, and served as the sensor cavity. One of the pipe sections was used as the sensing cavity. A propeller powered by a variable speed motor was inserted into the second pipe section and used to force flow through the sensor cavity. Two metal electrodes were attached to the outside of the sensory cavity pipe section on opposite sides of the pipe. These electrodes were connected with a capacitor (e.g., 10-47 pF) and an inductor (e.g., several turns, 0.4-inch diameter) to form a dielectric sensor as illustrated in FIG. 1.

Figure 5:
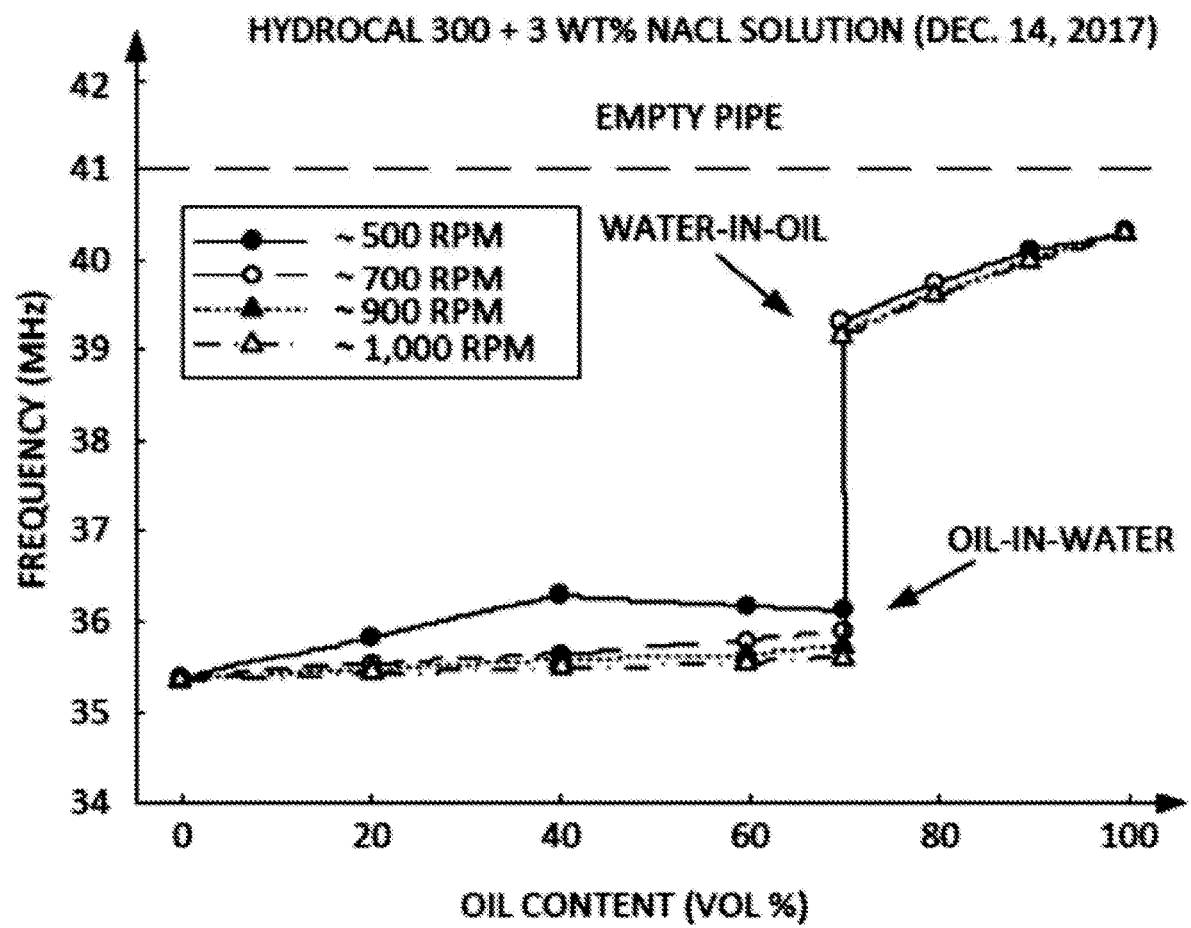
FIG. 5 is a graph showing the response of a dielectric sensor measured as resonance frequency versus oil content at different mixer speeds. The y-axis is frequency in MHz, and runs from 34 to 42 at increments of 1. The x-axis is oil content in vol %, and runs from 0 to 100 at increments of 20. The dotted line indicates the frequency response for an empty pipe.

FIG. 5 shows a typical response of the dielectric sensor for several mixtures of HYDROCAL 300 refined oil and 3 wt % solutions of Red Sea salt (mostly NaCl with some minerals characteristic of a marine environment), where oil+water equaled 100%. Each oil content mixture was tested at four values of mixer speed from 500 to 1,000 revolutions per minute (rpm). The minimum 500 rpm speed was chosen because it provided a uniform oil-water mixing without formation of small droplets or emulsion. The 1,000-rpm speed generated stable emulsions especially for oil content over 80%. The operating frequency was between 35 MHz and 41 MHz.

As it is clearly visible in FIG. 5, the resonance frequency versus oil content relation has two distinctive regimes. For mixtures above 70% oil content, the frequency is almost a linear function of oil content, as expected from the dielectric sensor principles. For these mixtures, the frequency versus oil content relation can be easily inversed thus allowing for calculation of oil content based on a measured resonance frequency. Importantly, for this part of the plot, the resonance frequency does not strongly depend on the mixer speed indicating low sensitivity to oil-water dispersion.

In contrast, mixtures with oil content below 70% generate very similar resonance frequency for all values of oil content with the exemption of data obtained at the lowest mixer speed of 500 rpm. This part of the frequency versus oil content relation cannot be reversed, meaning the oil content cannot be measured by the dielectric method for mixtures of this type. The response of the dielectric measurement shown in FIG. 5 does not appreciably improve with frequency. This was demonstrated in equivalent tests carried out at 90 MHz and 270 MHz that produced very similar results.

The two distinctive parts of data presented in FIG. 5 correlated with emulsion types observed during experiments. Oil-in-water mixtures or emulsions have much lower viscosity as compared to water-in-oil mixtures or emulsion. This difference of viscosity can be easily determined visually during experiments. All mixtures with oil content below 70% were low viscosity, therefore oil-in-water type. In contrast, all mixtures with oil content above 70% were viscous and of the water-in-oil type. Mixtures with 70% oil content can be of both types depending on how this oil content was achieved. Different oils behave differently when dispersed in water and the transition point between the two types of emulsions may be different, although it will generally occur between 30-80% oil content. Other factors like temperature, presence of dispersing additives or impurities, mixing conditions, and mixture history may also affect the transition point between the two mixture types. Finally, the transition is known to have significant hysteresis effect and not be very reproducible.

Figure 6:
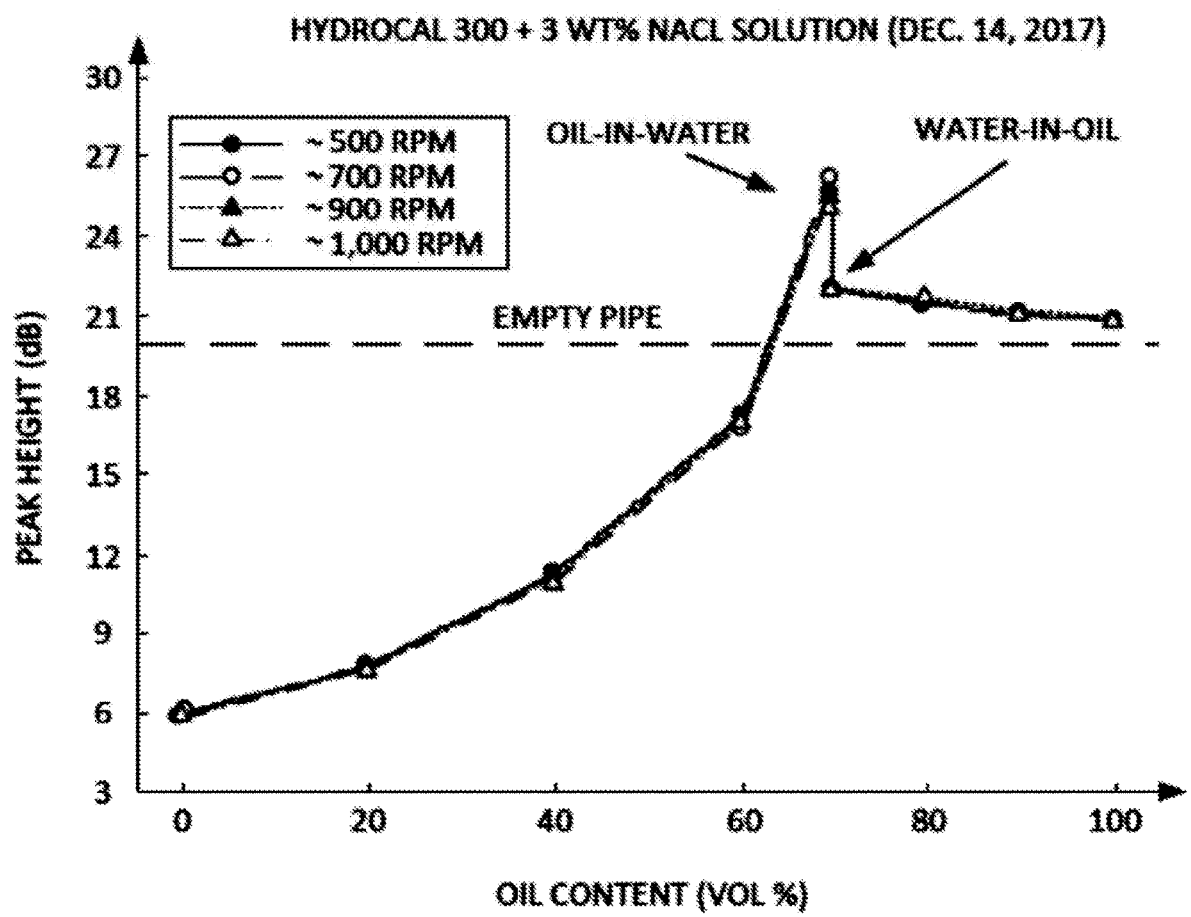
FIG. 6 is a graph showing the response of an eddy current sensor measured as peak resonance frequency height versus oil content at different mixer speeds. The resonance frequency was 21.72 MHz. The y-axis is peak height in decibels (dB), and runs from 3 to 30 at increments of 3. The x-axis is oil content in vol %, and runs from 0 to 100 at increments of 20. The dotted line indicates the peak height for an empty pipe.

The eddy current measurement was tested for the same range of oil-water mixtures as used in the dielectric measurements. The main quantity recorded during the eddy currents test was the height of a resonance peak. The resonance frequency was also recorded, however, it remained constant (21.72 MHz) for all mixtures as well as for an empty pipe measurement. FIG. 6 shows the response of the eddy current sensor to oil mixtures with different oil content and mixer speeds.

The response of the eddy currents sensor was measured as the height of the resonance peak. The peak height increased monotonically with oil content up to 70% and was independent of the mixer speed. The peak height dependence on oil content was quite strong, considering that the decibel scale is logarithmic. Together, FIG. 5 and FIG. 6 indicate that the dielectric and the eddy current measurements are complementary and, if used in conjunction in one sensor system, can provide a reliable oil content measurement for the entire range of oil-water mixtures.

It should be noted that the resonance frequency of the dielectric sensor (FIG. 5) changed from about 36 MHz for the oil-in-water mixtures to about 39 MHz for the water-in-oil mixtures. Thus, for example, resonance frequency values between 37 MHz and 38 MHz could be used by the sensor system to determine whether to report the dielectric sensor measurement or the eddy current sensor measurement (see FIG. 3).

Figure 7:
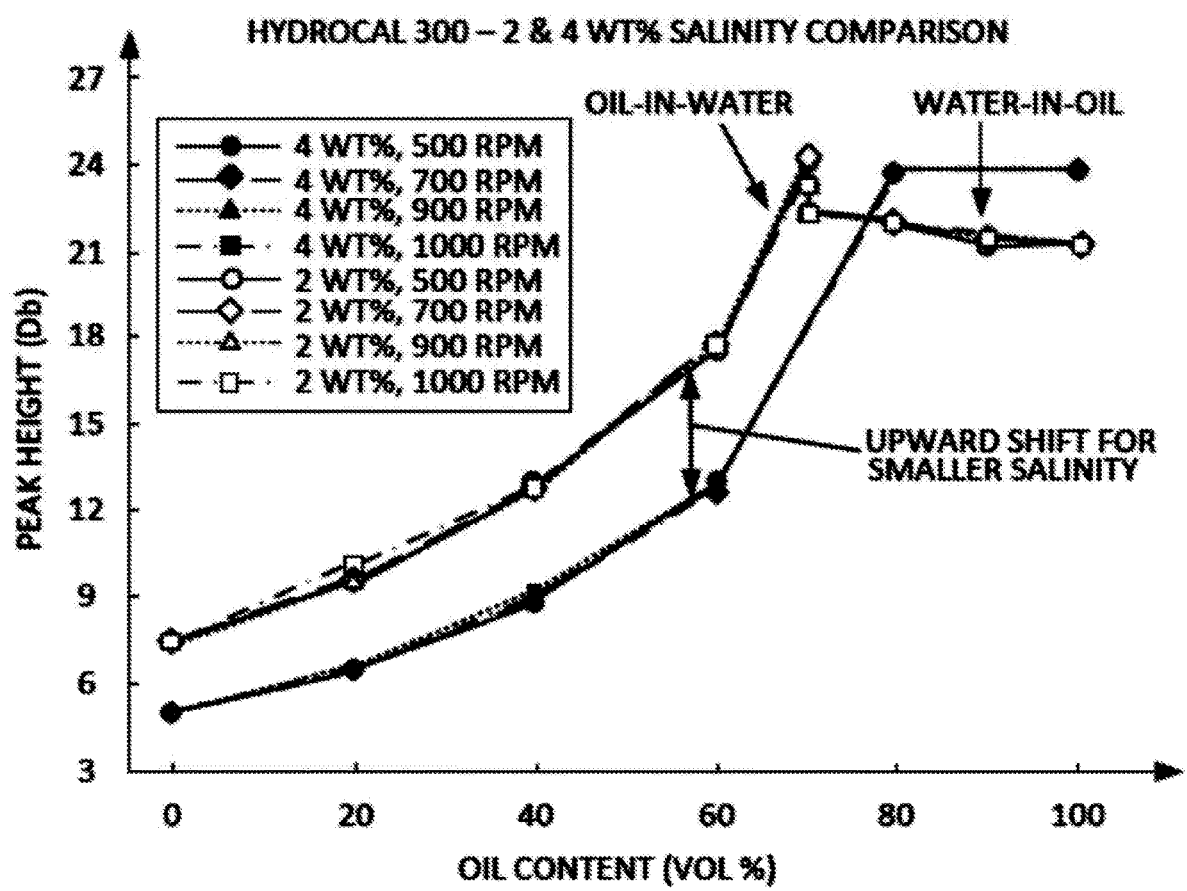
FIG. 7 is a graph showing the response of an eddy current sensor measured as resonance peak height versus oil content at different mixer speeds and different salinities (2 wt % and 4 wt %). The resonance frequency was 21.72 MHz. The y-axis is peak height in decibels (dB), and runs from 3 to 27 at increments of 3. The x-axis is oil content in vol %, and runs from 0 to 100 at increments of 20.

One important feature of the eddy current measurement is its dependence on water salinity. This is demonstrated in FIG. 7, which shows the eddy current signals obtained at 2 and 4 wt % water salinities.

Figure 8:
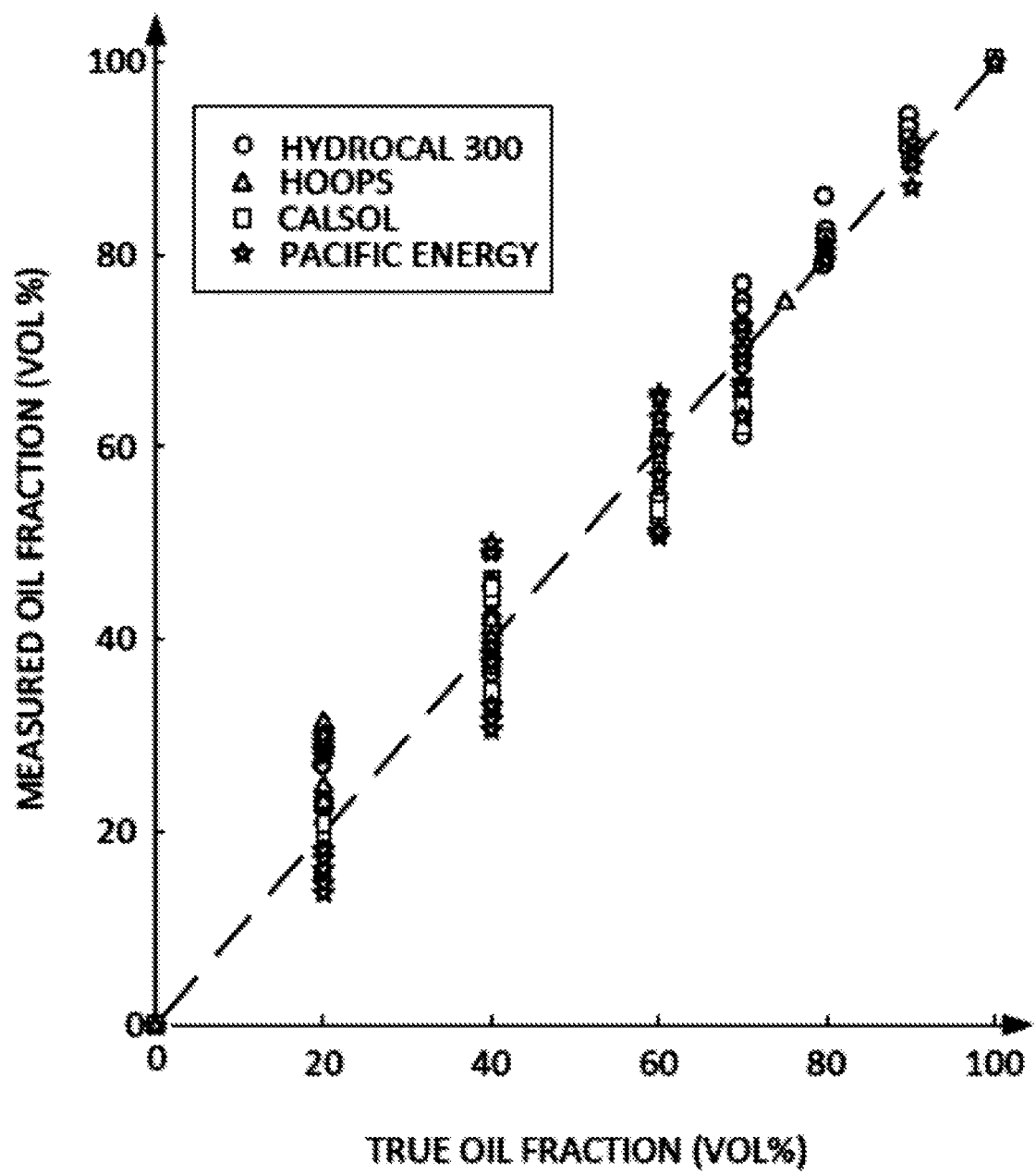
FIG. 8 shows the comparison between the measured oil fraction (based on algorithms described herein) and the true oil fraction, for showing the accuracy of the algorithm and sensor system. The y-axis is the measured oil fraction in vol %, and runs from 0 to 100 at increments of 20. The x-axis is the true oil fraction in vol %, and runs from 0 to 100 at increments of 20.

The effectiveness of combining a dielectric sensor with an eddy current sensor was tested for several types of oil, both refined and crude, and for salinity levels 2%, 3%, and 5%. FIG. 8 shows the comparison between true oil fraction and the oil fraction obtained from the combined sensor system. The agreement was excellent across the entire range of oil-water mixtures. Average error of measurement was below 3%, and the maximum error was below 12% (both measured in units of oil fraction). This level of accuracy is sufficient for oil recovery operations.

In addition, some embodiments, which are based on a combination of one dielectric sensor and one eddy current sensor, provide an accurate oil fraction information if the sensor cavity is fully filled with liquid oil-water mixture with no or only a minimum amount of air. However, if the tested stream contains a significant volume of air, or other gas or vapor, the sensor will interpret the gas volume as oil and effectively overestimate the oil fraction. This is particularly limiting for many types of oil recovery operations that produce streams containing a significant fraction of air and result in a "partially empty" condition in pipes and hoses used in these operations. A typical practice of oil recovery operations involves long and horizontal hoses or pipes and flow velocities that are too small to prevent flow stratification due to gravity. These conditions result in a stratified flow with oil-water mixture occupying the bottom part of the hose and air present on top.

Figure 15:
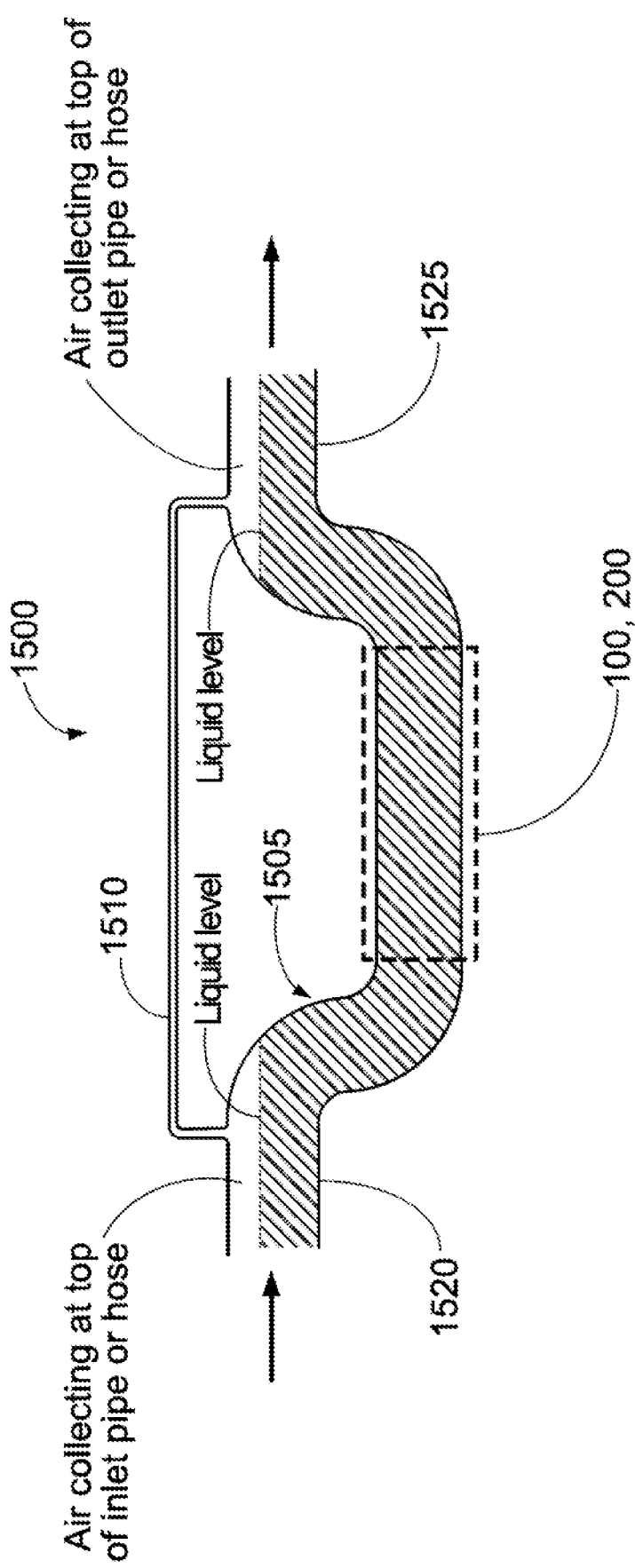
FIG. 15 shows an embodiment including an oil recovery sensor installed in a U-trap arrangement which ensures that the sensor cavity remains air-free.

An effective method to mitigate this adverse effect for sensors with streams containing air is to use a U-trap arrangement 1500, as shown in FIG. 15. In this arrangement, the sensors 100, 200 are installed below the inlet 1520 and outlet 1525 of the U-trap arrangement 1500, ensuring its cavity remains predominantly filled with liquids. In such an arrangement, passing air pockets are quickly displaced by buoyancy and spend relatively shorter time inside of the sensors 100, 200. This ensures that the effects of air are reduced, and the measured oil fraction is closer to its true value.

Embodiments relating to the U-trap method can be further improved if a second connection 1510 (e.g. an air passage) is installed at the top of the main U-trap 1505 to allow for air passage. This connection should be of smaller cross section since air has much lower viscosity as compared to oil or water. A smaller diameter connection will ensure relatively free flow of air but will restrict flow of liquids. For instance, for a 3- or 4-inch diameter sensor, and a ½ inch diameter air transfer connection may be used.

The example shown in FIG. 15 shows the U-trap design with the sensor mounted horizontally. However, this is not required. Any sensor orientation, including vertical, can be used. Still, the sensor mounted horizontally offers some benefits including: the overall height of the U-trap is minimized; the U-trap is less likely to trap solid impurities that may be present in the oil-water stream; and oil-water separation due to buoyancy is minimized. It should further be understood that, in the example of FIG. 15, the sensors 100, 200 may comprise any combination of sensor(s), including any number of dielectric sensor(s) 100 and/or any number of eddy current sensor(s) 200.

Some alternative embodiments use two dielectric measurements. As will be seen, these embodiments are particularly useful for measuring oil content in a horizontal pipe or hose which contains stratified water and oil layers as well as a significant volume of air. The two dielectric measurements may be carried out simultaneously with an eddy current measurement. The two dielectric measurements use different electrode geometries, one with the electrodes attached on sides of the sensor cavity, and the other with the electrodes attached at the sensor's top and bottom. The first electrode arrangement provides a measurement that is predominantly correlated with water content in the stream. The measurement using the top and bottom electrodes provides information about all three stream components. Information from both dielectric sensors can be used for a reliable determination of all three flow components in case where oil and water are stratified. The addition of a third measurement, based on the eddy current principle, further extends the capability of this sensor to flows where oil and water are well mixed or form emulsions.

The embodiments based on a combination of one dielectric sensor and one eddy current sensor provide an accurate oil fraction information if the sensor cavity is fully filled with liquid oil-water mixture with no or a minimum amount of air. However, if the tested stream contains a significant volume of air, or other gas or vapor, the sensor will interpret the gas volume as oil and effectively overestimate the oil fraction. This is a serious limitation for many types of oil recovery operations that produce streams containing a significant fraction of air and result in a "partially empty" condition in pipes and hoses used in these operations. Furthermore, a typical practice of oil recovery operations involves long and horizontal hoses or pipes and flow velocities that are too small to prevent flow stratification due to gravity. These conditions result in a three-layer flow with water occupying the bottom part of the hose, oil aggregating on top of water, and air present on top of both liquids.

Figure 9A:
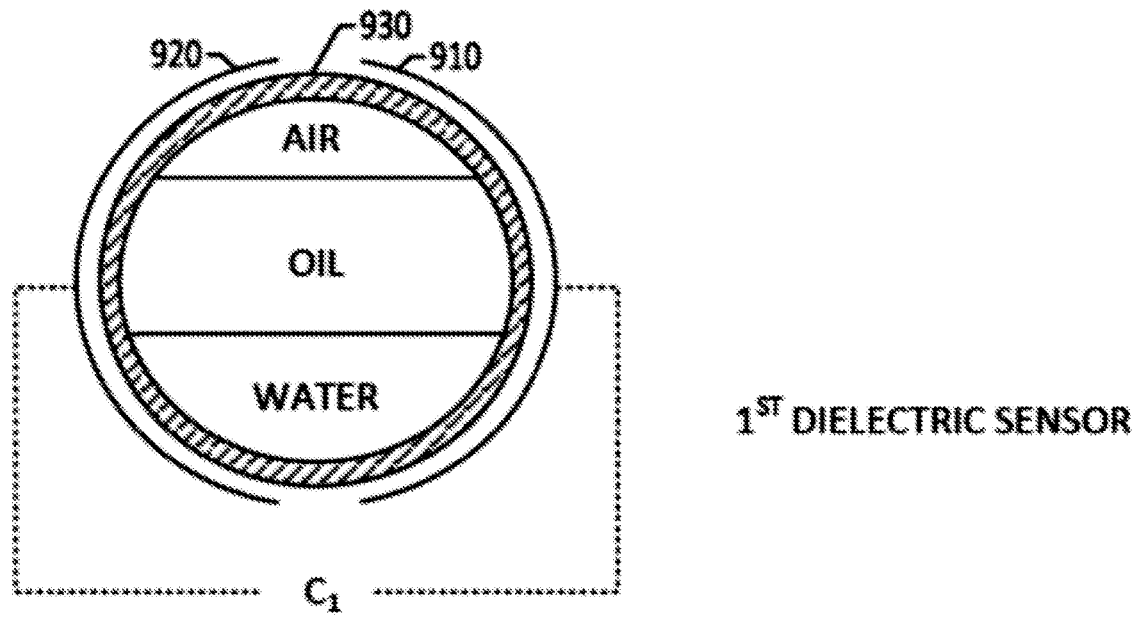
FIG. 9A shows an embodiment of a dielectric sensor with electrodes mounted on either side of the sensor cavity.
Figure 9B:
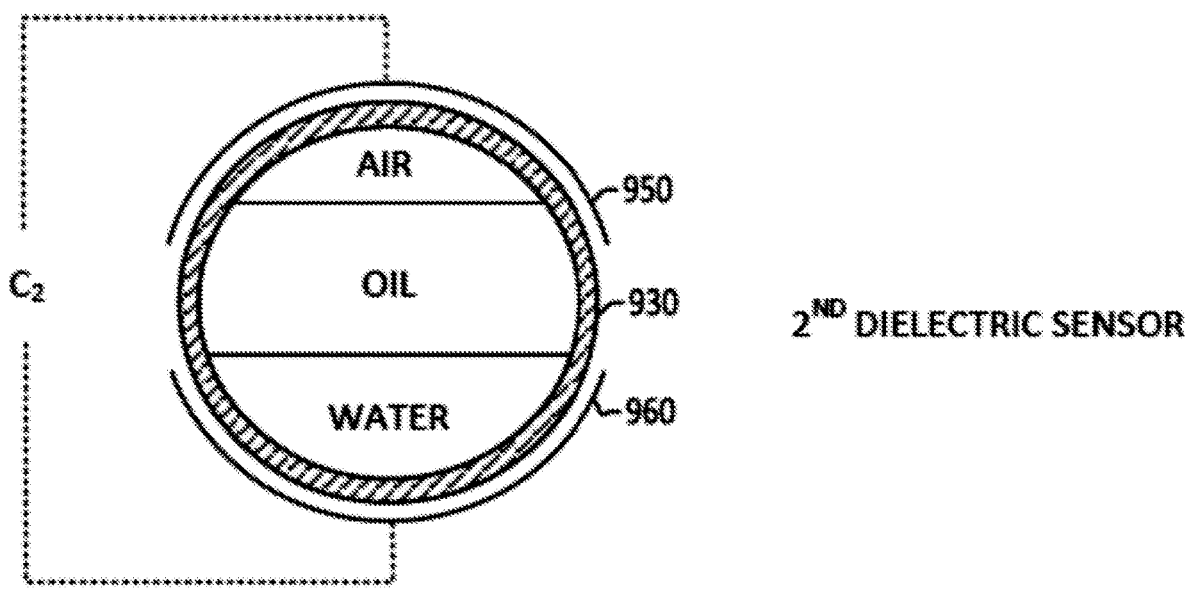
FIG. 9B shows an embodiment of a dielectric sensor with electrodes mounted on the top and bottom of the sensor cavity.

The embodiments which measure oil content in stratified flows containing air can be constructed using two dielectric measurements and one eddy current measurement. Some implementations use the gravity-induced stratification of all three components, or at least of the liquid and air, and apply two different electrode geometries for both dielectric measurements. FIG. 9A shows a first electrode arrangement with the first dielectric measurement using two electrodes 910, 920 attached on both sides of the sensor cavity. FIG. 9B shows a second electrode arrangement with the second dielectric measurement using one electrode 950 mounted at the sensor's top and another electrode 960 mounted at the sensor's bottom. These two electrode geometries will see the stratified oil-water-air streams differently and will provide different but complementary information about the stream composition. The difference between the two electrode configurations can be understood in terms of the well-known capacitance addition rules for capacitors connected in parallel and in series. In FIG. 9A, the electrodes 910, 920 mounted on both sides of the sensor cavity of the pipe 930 will see the three capacitances due to water, oil and air connected in parallel; therefore, the capacitance caused by the water layer will be the largest and dominant contribution to the effective capacitance. As a result, a signal from this measurement will be strongly correlated with the water layer fraction occupying the sensor cavity and almost independent of the oil and air fractions. In contrast, in FIG. 9B, the measurement using electrodes 950, 960 mounted at the top and bottom of sensor cavity will see the three capacitances being connected in series. In this case, the effective capacitance will be more strongly dependent on the air- and oil-layer, not only on the water layer. The combination of both measurements, while combined with an appropriate algorithm, will allow for simultaneous measurements of all three flow components and of the oil fraction in the liquid which can be calculated from these. The eddy currents measurement will still be needed for the analysis of streams where oil and water are well mixed and form a high conductivity oil-in-water type mixture or emulsion. For the reasons described previously, these high conductivity mixtures require the eddy currents measurement to measure their water and oil relative content.

Performance of the two combined dielectric sensor configurations, shown in FIGS. 9A and 9B, was demonstrated experimentally using mixtures of Hydrocal 300 oils and simulated seawater containing 3 wt % of salt. The tests were carried out using an acrylic schedule 40 pipe, 3 inches in diameter, and 2 feet long. The two sets of electrodes were constructed using an adhesive aluminum tape and connected with two resonance circuits operating in the 35-40 MHz range. The resonance frequencies were measured using the AA-170 SWR analyzer. Fractions of oil and water in the sensor pipe were changed in intervals of 10% of an internal pipe volume. Most of the possible water-oil fraction combinations were tested. All tests were carried out with the sensor pipe placed horizontally and after allowing the oil-water mixtures to separate and stratify during ~5 minutes period.

Figure 10:
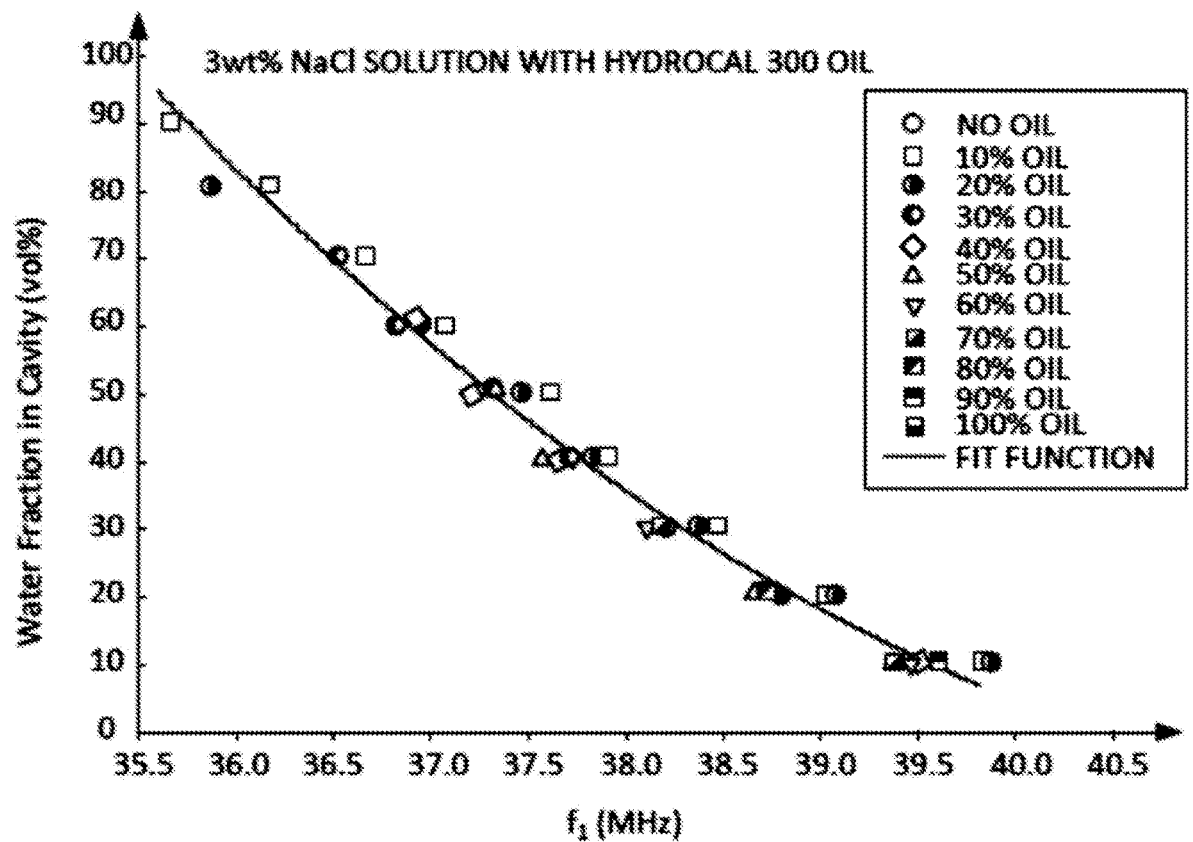
FIG. 10 illustrates the dependence between a water fraction in sensor's cavity and a first sensor output frequency.

The results of the test showed that the dielectric sensor using two side-mounted electrodes (e.g., as shown in FIG. 9A) produced a signal closely correlated with the water fraction in the sensor pipe. FIG. 10 shows the water fraction plotted as a function of the resonance frequency for this sensor. All experimental points follow one common function with a minimum deviation for different oil fraction values. To a good approximation, the water fraction in the sensor pipe (w) can be fitted to a quadratic function of frequency ($f_1$), with three constant parameters ($a_1$-$a_3$):

$$w = a_1 + a_2 f_1 + a_3 f_1^2 \quad (4)$$

Figure 11:
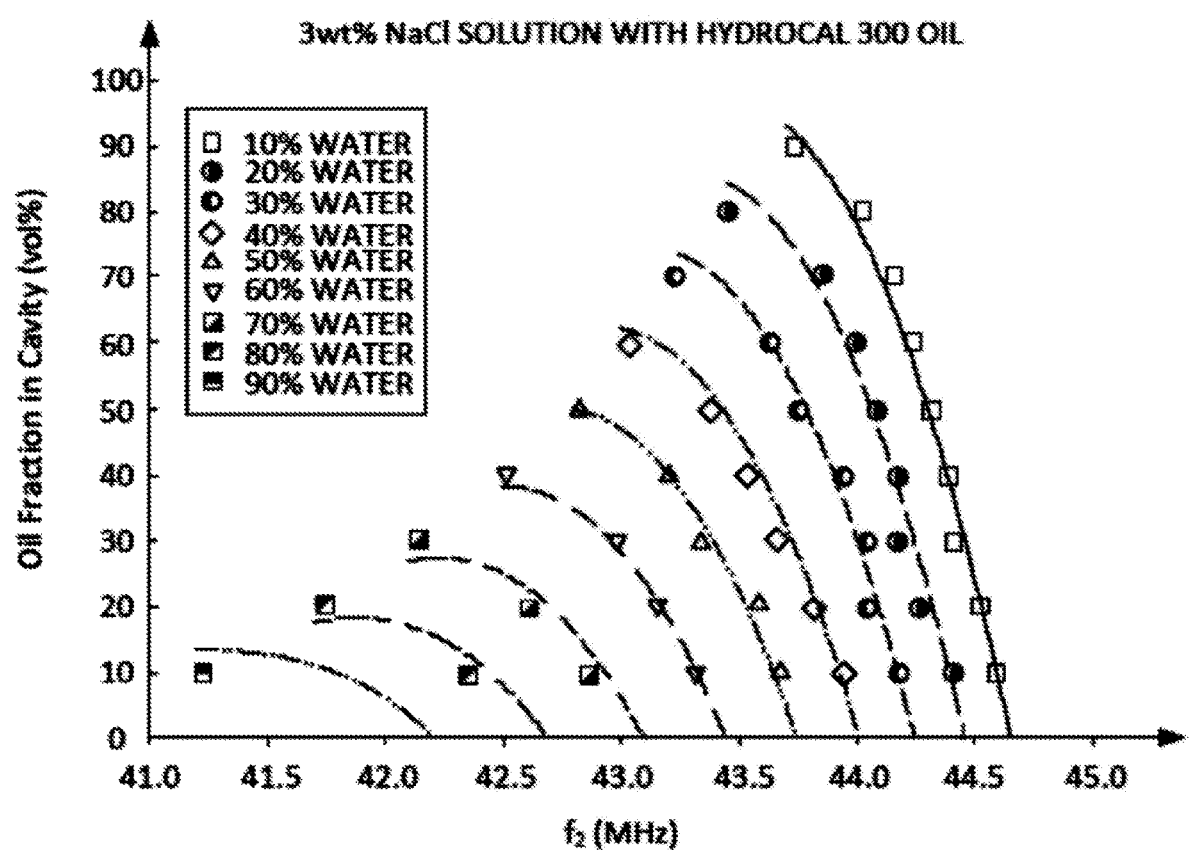
FIG. 11 illustrates the dependence between oil fraction in sensor's cavity and the second sensor output frequency for different water fraction.

The second dielectric measurement using the electrodes mounted on the top and bottom of the sensor cavity (e.g., as in FIG. 9B) is sensitive to both oil and water fractions. FIG. 11 presents the oil fraction plotted as a function of the resonance frequency for this sensor. In this case, instead of a single line, the experimental points follow separate lines for different water fractions. The oil fraction in the sensor (o) can be approximated as a function of the resonance frequency ($f_2$) and water fraction (w), obtained from the (Equation 4) expression above, and seven adjustable parameters ($b_1$-$b_7$):

$$o = b_1 + b_2 w + b_3 f_2 + b_4 w f_2 + b_5 w^2 + b_6 f_2^2 + b_7 f_2^3 \quad (5)$$

The lines shown in FIG. 11 were generated using this expression for water fractions in the 10-90% range. While expressions 4 and 5 provide representative descriptions of the experimental data, they are not unique, and many similar functions can be employed instead. More generally, the water fraction w can be determined using an empirical look-up table or empirical calibration function that receives the capacitance value measured by the first dielectric sensor (e.g., the capacitance value is frequency $f_1$ when using the first dielectric sensor of FIG. 9A), and likewise the oil fraction o can be determined using an empirical look-up table or empirical calibration function that receives the capacitance value measured by the second dielectric sensor (e.g., the capacitance value is frequency $f_2$ when using the second dielectric sensor of FIG. 9B) and also receives the water fraction w. The illustrative calibration function of Equation (4) is quadratic, but a linear, quadratic, cubic, or higher-order polynomial could be used, or some other empirical calibration function could be used (e.g. a fitted spline function). The illustrative calibration function of Equation (5) is cubic, but a linear, quadratic, cubic, or higher-order polynomial could be used, or some other empirical calibration function could be used (e.g. a fitted spline function).

Once the water- and oil-fraction inside the sensor cavity are obtained from (Equation 4) and (Equation 5), the oil fraction in the liquid stream (OF)—the quantity of interest for oil recovery operations—can be calculated as:

$$OF = \frac{o}{o + w} \quad (6)$$

Figure 12:
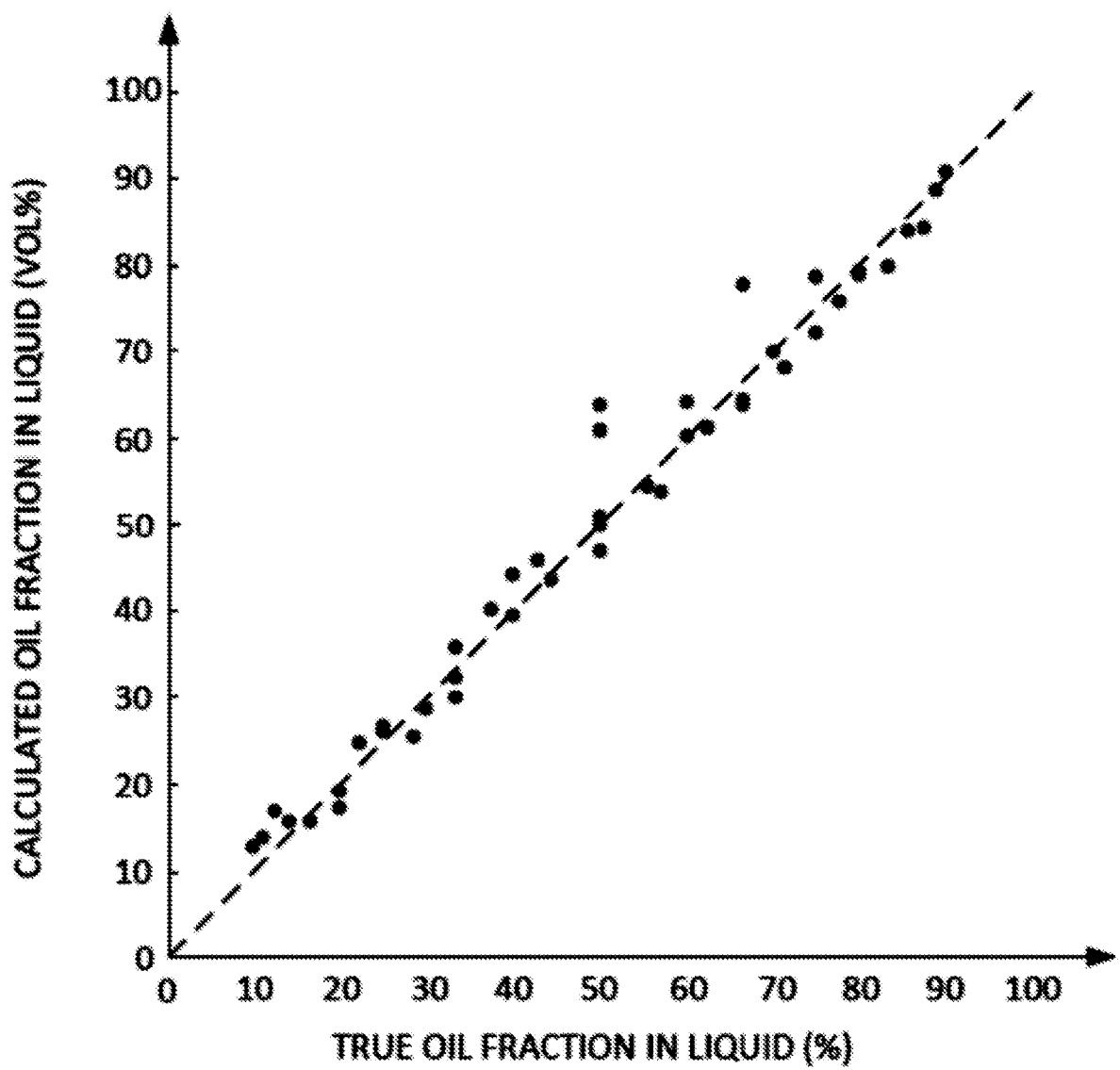
FIG. 12 illustrates correlations between calculated oil fractions and true oil fractions for the sensor implementation for stratified oil-water-air flows.

FIG. 12 demonstrates capabilities of an algorithm consisting of equations (Equations 4-6) as applied to the measurements described above. In other words, FIG. 12 shows the correlation between the oil fractions obtained from (Equations 4-6) and the true oil fractions. The calculated oil fraction values are very well correlated with the true oil fractions in the liquid. The correlation coefficient between the two measurement is over 0.987, the average error is about 3%, and the maximum error is about 14%. This accuracy is sufficient for the oil recovery application.

Figure 13:
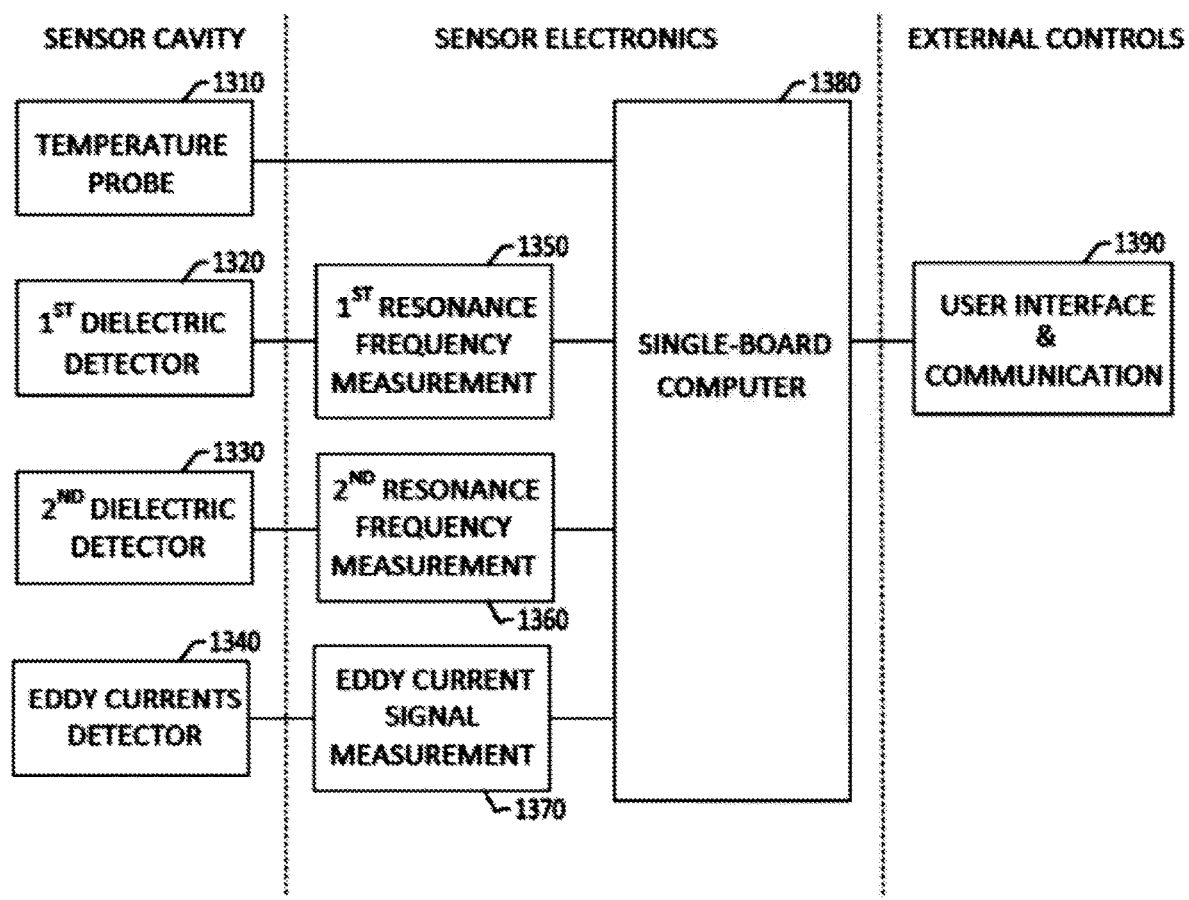
FIG. 13 illustrates an embedment of a sensor implementation for stratified oil-water-air flows.

At favorable oil-to-water ratios and for some oil types, these mixing conditions may generate uniform oil-water mixtures or emulsions instead of two separated liquid layers. As was discussed above, a dielectric detector alone is not able to properly analyze oil-water mixtures that are of oil-in-water type and contain water with high salinity of seawater. Such mixtures have very high electrical conductivity and tend to work not as dielectric media but as conductive electrodes. However, oil content of highly-conductive oil-in-water mixtures can be measured by an eddy current detector as described above. FIG. 13 presents an embodiment of a sensor implementation, which will measure oil fraction in liquid regardless of the air fraction in the stream, and regardless of oil-water mixing and dispersion conditions. This implementation will use two dielectric detectors 1320, 1330 with the two electrode geometries as shown in FIGS. 9A and 9B, respectively, one eddy current detector 1340, and a temperature probe 1310. The temperature measurement will be necessary to account for changes in electrical conductivity of water and allow for proper correction of the eddy current measurement 1370. FIG. 13 further illustrates a first resonant frequency measurement 1350 (also denoted as the frequency $f_1$) measured by the first dielectric detector 1320 (that is, the dielectric detector of FIG. 9A with the horizontally opposing electrodes 910, 920), second frequency measurement 1360 (also denoted as the frequency $f_2$) measured by the second dielectric detector 1330 (that is, the dielectric detector of FIG. 9B with the vertically opposing electrodes 950, 960), single-board computer 1380 and user interface & communication 1390. As noted previously, a dielectric sensor detects changes in electrical capacitance caused by different water content of the fluid in the cavity. Such changes are detected by a direct capacitance measurement, or often by a detection of a frequency shift of a resonance circuit which includes the cavity itself. Hence, the resonant frequency measurements 1350, 1360 for the respective first and second dielectric detectors 1320, 1330 may be represented by a capacitance value or other electrical circuit value representative of the frequency.

Figure 14:
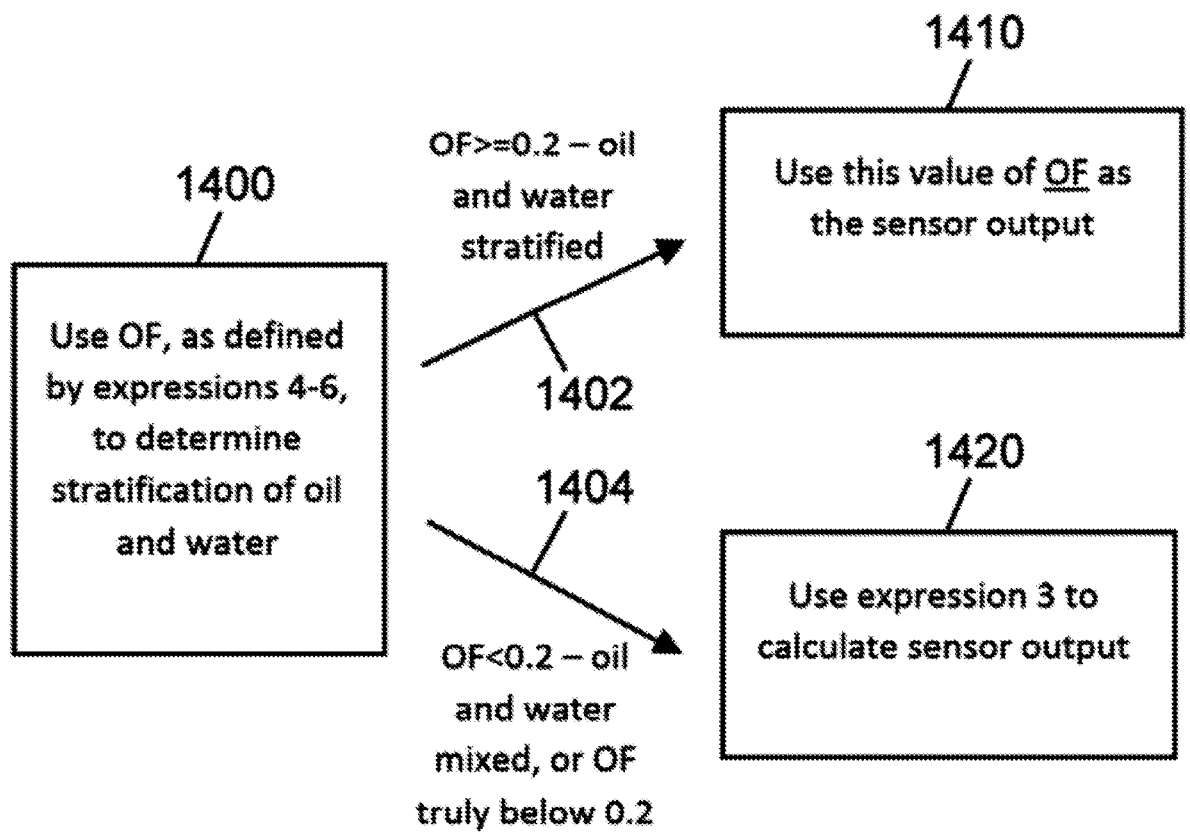
FIG. 14 illustrates components of an algorithm for calculation of oil content in a partially empty pipe based on combination of two dielectric measurements and one eddy current measurement.

FIG. 14 presents a method suitably performed by the computer 1380 (or, more generally, by an electronic processor). In an operation 1400, the oil fraction in the liquid stream (OF) is calculated as described in Equations 4-6 and is used to determine stratification of oil and water. If the oil and water are determined to be stratified at a decision branch 1402, then at an operation 1410 the oil fraction in the liquid stream (OF) is used as the oil sensor output. In the illustrative approach, decision branch 1402 determines the oil and water to be stratified if OF≥T, where T is some threshold value. In illustrative FIG. 14, T=0.2 so that the decision branch 1402 determines the oil and water to be stratified if OF≥0.2; however, more generally the threshold T may depend on flow characteristics in the pipe and can be determined empirically. It is expected that the threshold T will be 0.4 or lower in most cases, e.g. in the range 0.05≤T≤0.40 inclusive in some embodiments. On the other hand, if the oil and water are determined to be mixed at a decision branch 1404, then at an operation 1420 the oil sensor output is calculated using Equation 3. In the illustrative approach, decision branch 1404 determines the oil and water to be mixed if OF<T, where T is the threshold value also used in decision branch 1402. In illustrative FIG. 14, T=0.2 so that the decision branch 1404 determines the oil and water to be mixed if OF<0.2.

The data presented in FIGS. 10-12 were obtained in the static mode with both oil and water layers stagnant at the bottom of the sensor. The real application will involve unsteady flows and will be prone to forming waves and slugs that may cause at least partial mixing of oil and water. Effective measurements of unsteady flows will require multiple oil fraction tests carried out consecutively at a high rate, likely at least several measurements per second. Results of these measurements will need to be averaged over time with an appropriate time constant. It is expected that time constants from about one second up to several minutes will be appropriate for the oil recovery application. Two general approaches to time averaging will be described, but the application is not to be construed as being limited to these two approaches (e.g. additional approaches are contemplated). In one approach, measured resonant frequencies, the eddy current signal, and temperature can be averaged, and their average values will be used to calculate the oil content. In the second approach, the oil content for each instantaneous set of detector measurement will be calculated and the oil fraction values averaged over time.

The eddy current sensor and dielectric sensors of the foregoing embodiments employ an SWR analyzer. While this has advantages as disclosed herein, one potential drawback of using SWR analyzers is that commercially available high-speed SWR analyzers that are capable of performing multiple measurements per second are costly and may still have data acquisition speed limitations. The capacitance $C_1$ of the dielectric sensor of FIG. 9A and the capacitance $C_2$ of the dielectric sensor of FIG. 9B can be measured using a capacitance meter rather than the SWR-based resonant circuit of FIG. 1. For example, the capacitance meter can be a capacitance-to-digital converter implemented as an integrated circuit (IC). Some examples of such ICs include the FDC2×1× Capacitance-to-Digital Converters available from Texas Instruments (Dallas, Texas, USA). designed as low-noise capacitance-to-digital converters. The FDC2×1× family of ICs presently includes four members (FDC2112, FDC2114, FDC2212 and FDC2214) that differ in their conversion resolution and number of measurements channels. Advantageously, these ICs provide stable operation at broad range of temperatures (−40 to +125° C.), have high sensitivity (capacity resolution of 0.001 pF), and are relatively low-cost ICs (e.g., around $5-$10 per IC as of year 2020).

However, the eddy current sensor 200 of FIG. 2 is not amenable to implementation using a capacitance meter.

In the described two-sensor and three-sensor designs employing one or two dielectric sensors in combination with the eddy current sensor 200, the dielectric sensors are used if the oil content is above a threshold value, which may be the transition point between oil-in-water and water-in-oil mixtures or emulsions; whereas, the eddy current sensor 200 is used if the oil content is below the threshold value. Hence, the eddy current sensor 200 is advantageous for applications that benefit from measurement sensitivity at low oil fractions, such as some industrial oil and gas applications, or the application of triggering and monitoring operation of a mechanical surface skimmer to remove oil and oil-water mixtures from ocean surface water.

Figure 16:
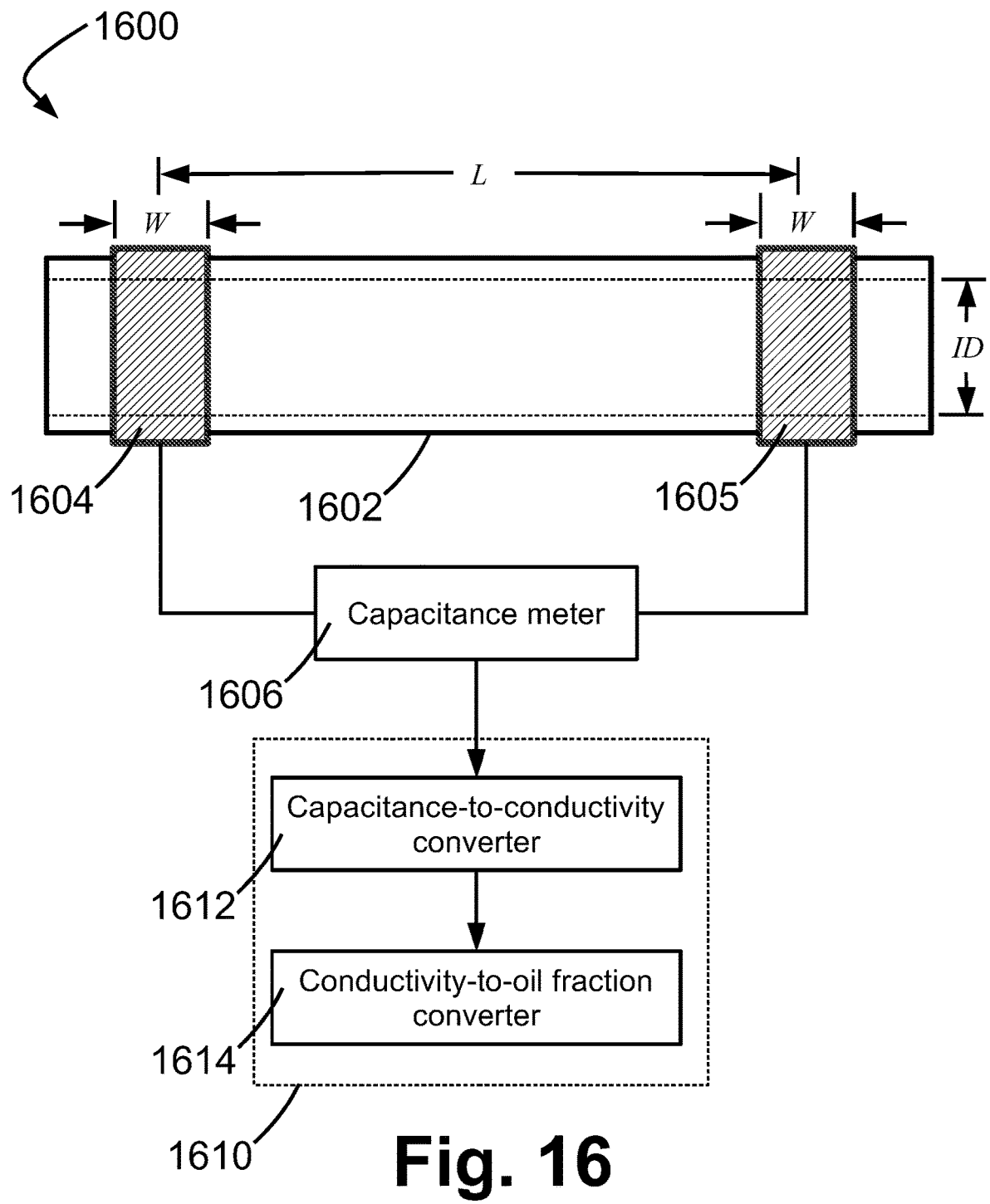
FIG. 16 shows an oil fraction sensor employing longitudinal capacitance measurement.

With reference to FIG. 16, an oil sensor 1600 is shown that, as demonstrated herein, provides sensitivity at low oil fractions, and hence can be employed alone for measuring oil content of a fluid, or can be employed in combination with one or two dielectric sensors to provide improved accuracy over the full 0-100% oil range. The illustrative oil sensor 1600 includes an electrically insulating channel 1602, which is typically an electrically insulating pipe 1602 such as, by way of non-limiting illustrative example: a plastic pipe, a polymer pipe, an acrylic pipe, a Teflon pipe, a fiberglass pipe, polyvinyl chloride (PVC) pipe, or so forth. A first electrode 1604 is disposed on an outside of the electrically insulating channel 1602, and a second electrode 1605 is also disposed on the outside of the electrically insulating channel 1602. The first electrode 1604 and the second electrode 1605 are spaced apart along the electrically insulating channel by a distance L. The illustrative electrically insulating pipe 1602 is straight at least over the distance L between the first electrode and the second electrode; however, curvature of the electrically insulating channel 1602 over the distance L between the first electrode and the second electrode is alternatively contemplated. The electrically insulating channel 1602 is preferably oriented horizontally in embodiments in which the fluid flow may include an overlying air layer. Moreover, it will be appreciated that the electrically insulating channel may take the form from the U-trap 1500 of FIG. 15, for example with the electrically insulating channel 1602 including a straight pipe portion having a length greater than or equal to the distance L, and bent pipe portions at the ends of the straight pipe portion whereby the electrically insulating pipe defines a U-trap. In this embodiment, the first and second electrodes 1604, 1605 may each be attached to the outside of the straight pipe portion.

Each electrode 1604, 1605 may comprise an electrically conductive ring of width W as indicated in FIG. 16. For example, each electrically conductive ring electrode may comprise copper foil adhered to or otherwise disposed on the outside of the electrically insulating pipe. Other non-limiting examples of suitable electrode materials include other metal or metal alloy foils, deposited metal or metal alloy layers, conductive carbon film layers, or so forth. Each electrically conductive ring in the illustrative example has a width W and completely encircles the outside of the electrically insulating pipe 1602. However, in variant embodiments, each electrode 1604, 1605 may only partially encircle the outside of the electrically insulating pipe 1602.

The sensor 1600 of FIG. 16 further includes a capacitance meter 1606 that is connected to measure the capacitance between the first electrode 1604 and the second electrode 1605. In general, any type or implementation of capacitance meter can be employed as the capacitance meter 1606. In a preferred embodiment, the capacitance meter 1606 is a capacitance-to-digital converter implemented as an IC, such as one of the family of FDC2×1× Capacitance-to-Digital Converters available from Texas Instruments. The capacitance meter 1606 is configured to measure the capacitance between the first electrode 1604 and the second electrode 1605 at a frequency that is preferably in a range of 10 kHz to 10 MHz, and more preferably in a range of 1 MHz to 10 MHz, although operation outside of these illustrative frequency ranges is also contemplated.

Figure 17:
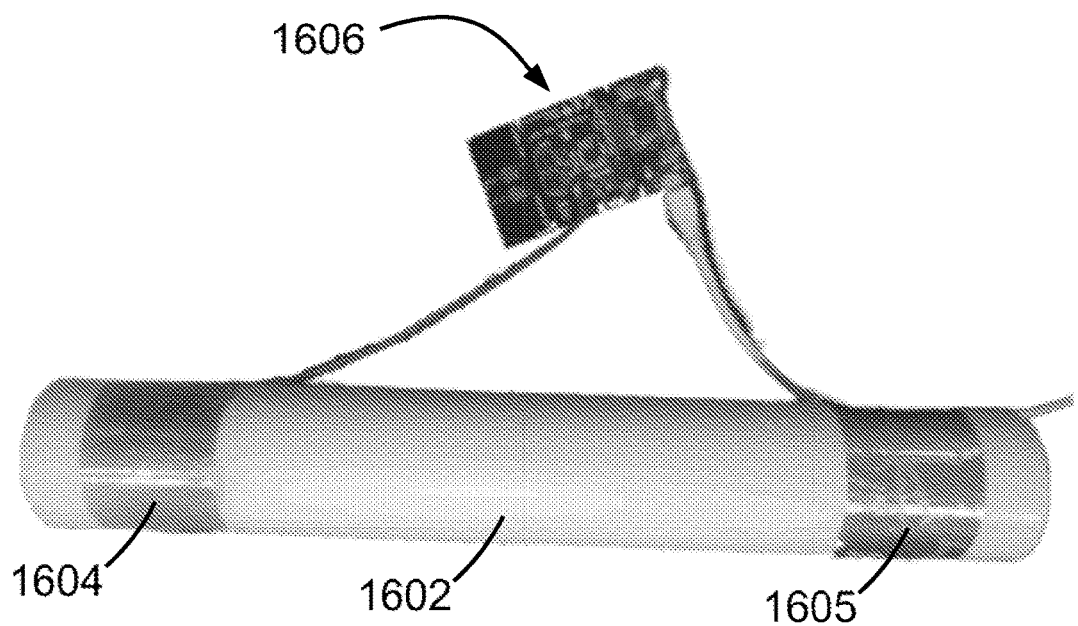
FIG. 17 shows an experimental oil fraction sensor constructed in accordance with the design of FIG. 16 (top), and a table of conductivity measurements (bottom) obtained using the experimental oil fraction sensor.

With brief reference to FIG. 17, an implementation of the sensor 1600 of FIG. 16 as described above has been constructed and tested. As shown in the top part of FIG. 16, a section of 2-inch, schedule 40, polyvinyl chloride (PVC) pipe was employed as the electrically insulating channel 1602, and was fitted with two electrodes 1604, 1605 made of an adhesive copper foil. Each electrode formed a 2-inch wide ring (i.e., the width W=2-inch) going around a circumference of the pipe 1602. The distance L between the electrodes, measured between their centers, was 10-inches. The electrodes were connected with a FDC2214EVM evaluation board to provide the capacitance meter 1606. (The FDC2214EVM evaluation board includes an FDC2214 Capacitance-to-Digital Converter mounted on a printed circuit board (PCB) with ancillary electronics). The table presented in the bottom part of FIG. 16 shows values of capacitance measured for different fluids inside the sensor pipe 1602. The measurements were carried out with the two non-conductive fluids: air (that is, an empty pipe) and with the pipe filled with mineral oil. These two measurements produced almost identical values of capacitance (28.906 pF for the empty pipe and 28.953 pF for the mineral oil-filled pipe). By sharp contrast, the measurements carried out with conductive fluids, namely a 1 wt % NaCl-in-water solution and a 5 wt % NaCl-in-water solution, indicated much larger values of capacitance that were progressively larger at higher salinities (46.790 pF for the 1 wt % solution and 52.804 pF for the 5 wt % solution). These results demonstrate that the electrode geometry of the sensor 1600 of FIG. 16 measures electrical conductivity of fluid within the sensor pipe, which is similar in functionality to the eddy current measurement described previously. The 1 wt % and 5 wt % solutions are representative of the electrical conductivities of low oil-in-water solutions. Thus, these experimental results also demonstrate that the sensor 1600 of FIG. 16 has high sensitivity at low oil fractions, making it a suitable substitute for the eddy current sensor 200 in the two- or three-sensor embodiments.

With returning reference to FIG. 16, given the geometry of the sensor 1600 including the inner diameter ID of the electrically insulating pipe 1602 and the electrodes separation L, one or more processors 1610 (e.g. an electronic microprocessor or microcontroller) determine an oil content of the fluid contained in the electrically insulating pipe 1602 based on the capacitance between the first electrode 1604 and the second electrode 1605 as measured by the capacitance meter 1606. In the illustrative example, this is done in two steps. First, a capacitance-to-conductivity converter 1612 implemented by the one or more processors 1610 converts the capacitance between the first and second electrodes 1604, 1605 measured by the capacitance meter 1606 to an electrical conductivity of the fluid contained in the electrically insulating channel 1602 based on at least the measured capacitance and the distance L. For example, the equivalent circuit model described in chapter 15 of Paul Delahay, "New Instrumental Methods in Electrochemistry" Interscience Publishers Inc. 1954 can be used for this conversion. Then, a conductivity-to-oil fraction converter 1614 implemented by the one or more processors 1610 determines the oil content of the fluid contained in the electrically insulating channel 1602 based on the electrical conductivity of the fluid contained in the electrically insulating channel 1602. This can be done empirically, by measuring the electrical conductivities of oil-and-water mixtures of different oil fractions to generate an empirical look-up table or fitted empirical formula (e.g., a polynomial formula) for determining the oil content from the electrical conductivity.

Figure 18:
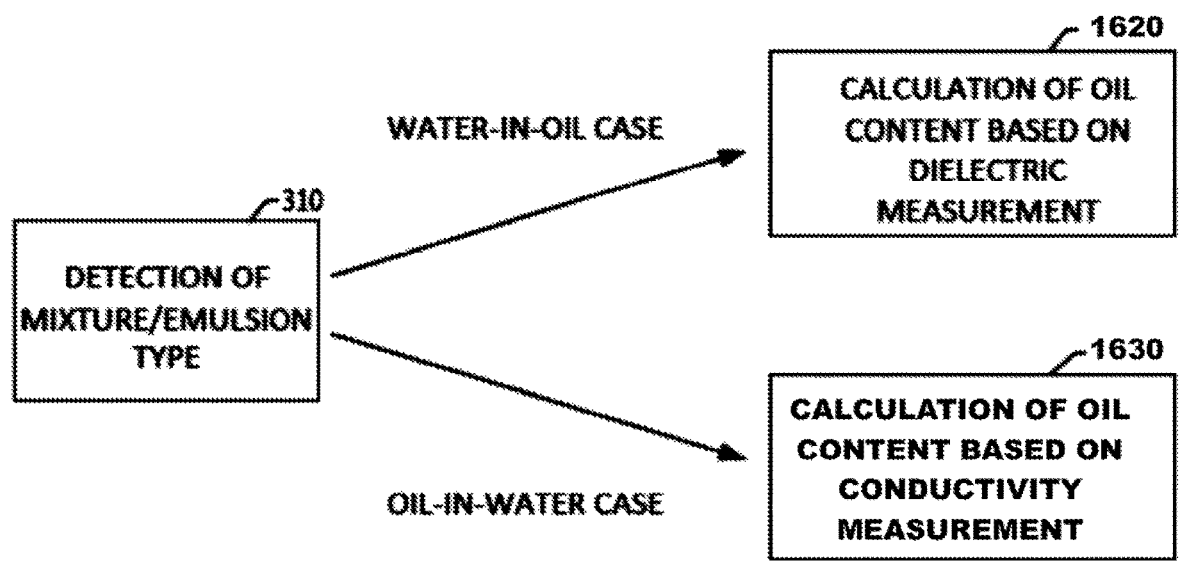
FIG. 18 corresponds to FIG. 3 but employs capacitance meters and the conductivity sensor of FIG. 16.

With reference to FIG. 18, the oil fraction sensor 1600 of FIG. 16 can be advantageously combined with at least one dielectric sensor (e.g., the horizontally oriented dielectric sensor of FIG. 9A, and/or the vertically oriented dielectric sensor of FIG. 9B). This is depicted in FIG. 18, which is analogous to FIG. 3 except that the operation 1620 of FIG. 18 which replaces the operation 320 of FIG. 3 preferably uses a capacitance meter to measure the capacitance(s) of the dielectric sensor(s), and the operation 1630 of FIG. 18 which replaces the operation 330 of FIG. 3 calculates the oil content based on a conductivity measurement performed using the sensor 1600 of FIG. 16.

Figure 19:
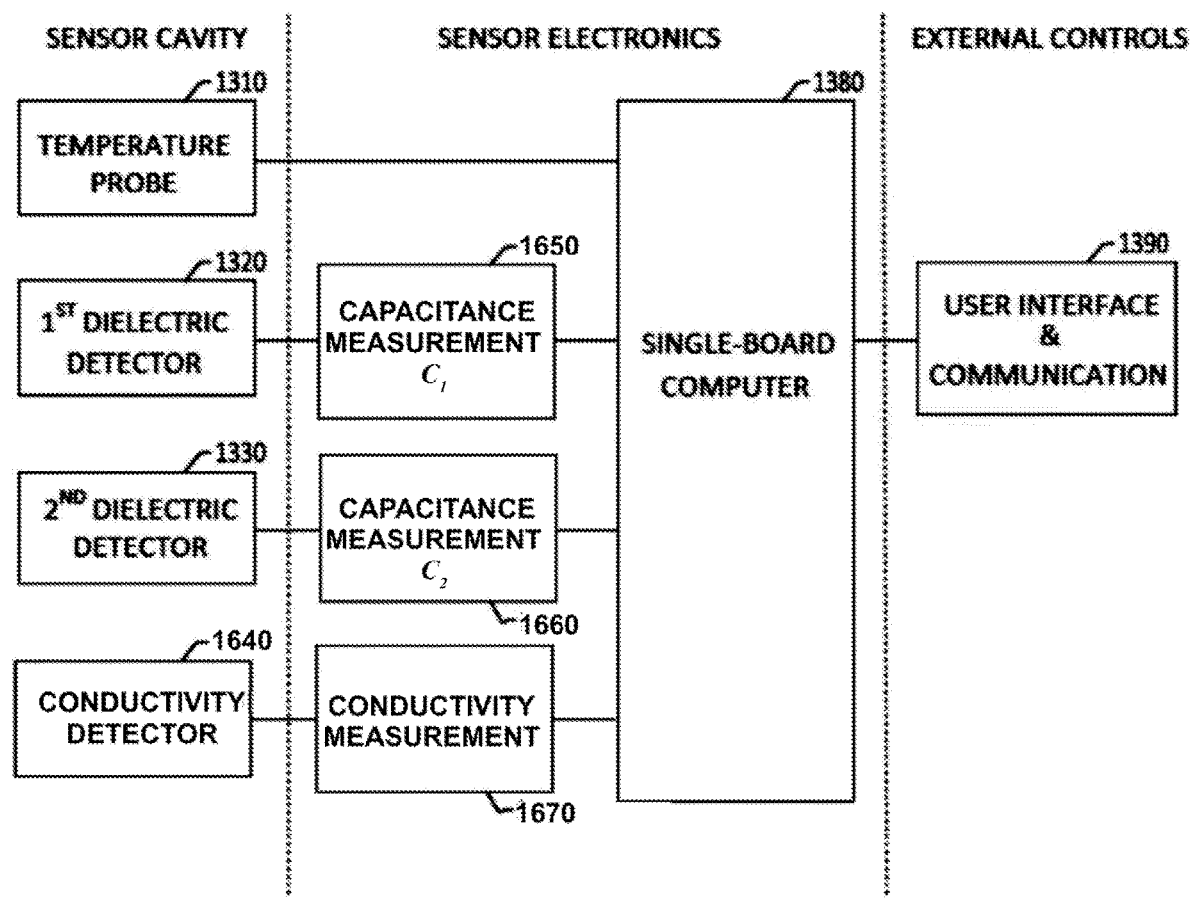
FIG. 19 illustrates an embedment of a sensor implementation for stratified oil-water-air flows analogous to that of FIG. 13 but employing capacitance meters and the conductivity sensor of FIG. 16.

With reference to FIG. 19, the embedment of a sensor implementation for stratified oil-water-air flows of FIG. 13 is shown. The system of FIG. 19 is identical with that of FIG. 13, except that the dielectric detectors 1330, 1340 in the embodiment of FIG. 19 preferably employ capacitance meters to measure capacitances $C_1$ 1650 and $C_2$ 1660 indicated in respective FIGS. 9A and 9B, and the eddy current detector 1340 which acquires the eddy current signal measurement 1370 in FIG. 13 is replaced by an electrical conductivity detector 1640 suitably comprising the electrically insulating pipe 1602, electrodes 1604, 1605, and capacitance meter 1606 as shown in FIG. 16 which acquires a conductivity measurement 1670.

Advantageously, the embodiments of FIGS. 18 and 19 employ capacitance meters in place of the SWR analyzers of earlier embodiments. In one suitable approach, a multi-channel capacitance-to-digital converter implemented as an IC (for example a single FDC2×1× Digital to Capacitance Converter) is used. In this approach, the capacitance meter 1606 of the sensor 1600 of FIG. 16 and the (dielectric sensor) capacitance meter of each dielectric sensor are implemented using respective channels of the multi-channel capacitance-to-digital converter.

The present disclosure has been described with reference to exemplary embodiments. Modifications and alterations may occur to others upon reading and understanding the preceding detailed description. It is intended that the present disclosure be construed as including all such modifications and alterations insofar as they come within the scope of the appended claims or the equivalents thereof.

The invention claimed is:

1. A system for measuring oil content of a fluid, the system comprising:
   an electrically insulating channel;
   a first electrode disposed on an outside of the electrically insulating channel;
   a second electrode disposed on the outside of the electrically insulating channel, wherein the first electrode and the second electrode are longitudinally spaced apart along the electrically insulating channel by a longitudinal distance L;

a capacitance meter connected to measure capacitance between the first electrode and the second electrode; and one or more processors configured to determine an oil content of a fluid contained in the electrically insulating channel based on the measured capacitance between the first electrode and the second electrode.

2. The system of claim 1 wherein:

the electrically insulating channel comprises an electrically insulating pipe;

the first electrode at least partially encircles the outside of the electrically insulating pipe; and the second electrode at least partially encircles the outside of the electrically insulating pipe.

3. The system of claim 2 wherein the electrically insulating pipe is straight at least over the longitudinal distance L between the first electrode and the second electrode.

4. The system of claim 2 wherein the electrically insulating pipe includes:

a straight pipe portion having a length greater than or equal to the longitudinal distance L wherein the first electrode is disposed on the outside of the straight pipe portion and the second electrode is disposed on the outside of the straight pipe portion;

bent pipe portions at opposite ends of the straight pipe portion whereby the electrically insulating pipe defines a U-trap; and an air passage at the top of the U-trap and connecting the bent pipe portions, the air passage being of smaller cross section than the straight pipe portion.

5. The system of claim 2 wherein the capacitance meter comprises a capacitance-to-digital converter implemented as an integrated circuit (IC).

6. The system of claim 2 further comprising:

at least one dielectric sensor, wherein each dielectric sensor includes:

a first dielectric sensor electrode disposed on the outside of the electrically insulating pipe;

a second dielectric sensor electrode disposed on the outside of the electrically insulating pipe, wherein the first dielectric sensor electrode and the second dielectric sensor electrode are disposed on radially opposite sides of the electrically insulating pipe; and a dielectric sensor capacitance meter connected to measure a capacitance between the first dielectric sensor electrode and the second dielectric sensor electrode;

wherein the one or more processors are configured to determine the oil content of the fluid contained in the electrically insulating channel further based on the measured capacitance between the first dielectric sensor electrode and the second dielectric sensor electrode.

7. The system of claim 6 wherein at least one dielectric sensor includes:

a vertically oriented dielectric sensor in which the first and second dielectric sensor electrodes are spaced apart vertically; and a horizontally oriented dielectric sensor in which the first and second dielectric sensor electrodes are spaced apart horizontally.

8. The system of claim 6 comprising a multi-channel capacitance-to-digital converter implemented as an integrated circuit (IC), wherein the capacitance meter and the dielectric sensor capacitance meter of each dielectric sensor are implemented using respective channels of the multi-channel capacitance-to-digital converter.

9. The system of claim 2 wherein:

the first electrode comprises a first electrically conductive ring completely encircling the outside of the electrically insulating pipe; and the second electrode comprises a second electrically conductive ring completely encircling the outside of the electrically insulating pipe.

10. The system of claim 1 wherein the one or more processors are configured to determine the oil content of the fluid contained in the electrically insulating channel based on the measured capacitance between the first electrode and the second electrode and further based on a salinity of a water component of the fluid contained in the electrically insulating channel.

11. The system of claim 1 wherein the one or more processors are configured to determine the oil content of the fluid contained in the electrically insulating channel based on the measured capacitance between the first electrode and the second electrode and further based on the longitudinal distance L.

12. The system of claim 1 wherein the one or more processors are configured to determine the oil content of the fluid contained in the electrically insulating channel by operations including:

converting the measured capacitance between the first and second electrodes to an electrical conductivity of the fluid contained in the electrically insulating channel based on the measured capacitance and the longitudinal distance L; and determining the oil content of the fluid contained in the electrically insulating channel based on the electrical conductivity of the fluid contained in the electrically insulating channel.

13. The system of claim 1 wherein the capacitance meter is configured to measure the capacitance between the first electrode and the second electrode at a frequency in a range of 10 kHz to 10 MHz.

14. The system of claim 1 comprising:

a capacitance measurement device including the capacitance meter, the first electrode, and the second electrode;

wherein the capacitance measurement device does not include any other electrode besides the first electrode and the second electrode.

15. A method for measuring oil content of a fluid, the method comprising:

disposing a mixture of oil and water in an electrically insulating channel; and determining an oil content of the mixture of oil and water in the electrically insulating channel by operations including:

using a capacitance meter, measuring a capacitance between a first electrode and a second electrode wherein the first electrode is disposed on an outside of the electrically insulating channel, the second electrode is disposed on the outside of the electrically insulating channel, and the first electrode and the second electrode are spaced apart along the electrically insulating channel by a distance L; and using one or more processors, determining an oil content of the mixture of oil and water in the electrically insulating channel based on the measured capacitance between the first electrode and the second electrode and further based on the distance L.

16. The method of claim 15 wherein the capacitance meter comprises a capacitance-to-digital converter implemented as an integrated circuit (IC).

17. The method of claim 15 wherein the oil content of the fluid contained in the electrically insulating channel is determined further based on a salinity of a water component of the mixture of oil and water in the electrically insulating channel.

18. The method of claim 15 wherein the electrically insulating channel comprises an electrically insulating pipe.

19. The method of claim 15 wherein the disposing of the oil and water in the electrically insulating channel comprises obtaining the mixture of oil and water by performing oil recovery comprising mechanical surface skimming.

20. The method of claim 19 wherein the electrically insulating channel comprises an electrically insulating pipe and the disposing comprises flowing the mixture of oil and water through the electrically insulating pipe while determining the oil content of the mixture of oil and water.

* * * * *